US012631631B2

(12) United States Patent
Schaefer et al.

(10) Patent No.: US 12,631,631 B2
(45) Date of Patent: May 19, 2026

(54) CHROMATOGRAPHIC READER DEVICES FOR BIODETECTION

(71) Applicant: 3M INNOVATIVE PROPERTIES COMPANY, St. Paul, MN (US)

(72) Inventors: Antonia E. Schaefer, Lake Elmo, MN (US); Nicholas T. Gabriel, Grand Rapids, MN (US); Samuel J. Fahey, Woodbury, MN (US); Adam C. Nyland, St. Paul, MN (US); Thaine W. Fuller, Lakeland, MN (US); John M. Kruse, Minneapolis, MN (US); Nicholas G. Amell, Burnsville, MN (US); Glendon D. Kappel, Minneapolis, MN (US); Patrick A. Mach, Shorewood, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 326 days.

(21) Appl. No.: 18/024,139

(22) PCT Filed: Aug. 18, 2021

(86) PCT No.: PCT/IB2021/057613
§ 371 (c)(1),
(2) Date: Mar. 1, 2023

(87) PCT Pub. No.: WO2022/049437
PCT Pub. Date: Mar. 10, 2022

(65) Prior Publication Data
US 2023/0266314 A1      Aug. 24, 2023

Related U.S. Application Data

(60) Provisional application No. 63/074,825, filed on Sep. 4, 2020.

(51) Int. Cl.
*G01N 33/543* (2006.01)
*G06T 7/00* (2017.01)

(52) U.S. Cl.
CPC ..... *G01N 33/54388* (2021.08); *G06T 7/0014* (2013.01)

(58) Field of Classification Search
CPC ............. G01N 33/54388; G01N 21/78; G01N 33/54387; G01N 21/8483; G01N 2021/7759; G06T 7/0014
See application file for complete search history.

(56) References Cited

U.S. PATENT DOCUMENTS 5,968,839 A * 10/1999 Blatt ................ G01N 33/54388
435/11
6,235,241 B1 5/2001 Catt et al.
(Continued)

FOREIGN PATENT DOCUMENTS

CN 103499687 A 1/2014
CN 204392399 U 6/2015
(Continued)

OTHER PUBLICATIONS

International Search Report for PCT International Application No. PCT/IB2021/057612, mailed on Nov. 24, 2021, 4 pages.
(Continued)

*Primary Examiner* — Mohamed K Amara
(74) *Attorney, Agent, or Firm* — Philip P. Soo

(57) ABSTRACT

An apparatus comprising a mobile computing device (902) physically coupled to a lightbox (904). The apparatus includes camera hardware, processing circuitry in communication with the camera hardware, and an interface in communication with the processing circuitry. The camera hardware is configured to capture image data associated with an output signal area of a biological chromatographic test
(Continued)

strip (410) inserted into a receiving slot of the lightbox. The processing circuitry is configured to determine, based on the image data captured by the camera hardware, a concentration of a target analyte in a test sample submitted via the biological chromatographic test strip. The interface is configured to output data indicative of the concentration of the target analyte determined by the processing circuitry.

18 Claims, 31 Drawing Sheets

(56)                    References Cited

U.S. PATENT DOCUMENTS

| | | | |
|---|---|---|---|
| 7,297,528 | B2 | 11/2007 | Takaiwa et al. |
| 8,089,623 | B2* | 1/2012 | Kao ...................... B01L 3/5025 356/417 |
| 8,889,427 | B2 | 11/2014 | Altschul et al. |
| 9,063,091 | B2* | 6/2015 | Tsai ........................ G06F 18/22 |
| 9,194,859 | B2 | 11/2015 | Emeric et al. |
| 9,335,290 | B2 | 5/2016 | Ewart et al. |
| 9,476,879 | B2 | 10/2016 | Ma et al. |
| 9,789,483 | B2 | 10/2017 | Khattak et al. |
| 9,858,684 | B2* | 1/2018 | Kim ........................... G06T 7/85 |
| 10,534,009 | B2* | 1/2020 | Holmes .................. G01N 35/04 |
| 11,061,026 | B2* | 7/2021 | Beckley ................. G01N 33/76 |
| 11,307,147 | B2* | 4/2022 | Lu ........................... G01N 21/80 |
| 11,988,596 | B2* | 5/2024 | Marcelpoil ...... G01N 33/54388 |
| 2002/0055126 | A1* | 5/2002 | Schaffler .......... G01N 33/54388 435/7.9 |
| 2004/0053423 | A1* | 3/2004 | LaBorde .............. G01N 33/585 436/514 |
| 2004/0203086 | A1* | 10/2004 | Piasio ............. G01N 33/54326 435/11 |
| 2005/0026302 | A1* | 2/2005 | Qian .................... G01N 33/525 436/514 |
| 2006/0008923 | A1* | 1/2006 | Anderson ............. G16H 15/00 702/19 |
| 2006/0222567 | A1* | 10/2006 | Kloepfer ............ G01N 21/8483 422/68.1 |
| 2006/0281187 | A1* | 12/2006 | Emery ............. A61B 5/150358 436/169 |
| 2007/0231922 | A1* | 10/2007 | Petruno ............. G01N 21/8483 436/514 |
| 2008/0274565 | A1 | 11/2008 | Samake et al. |
| 2010/0113285 | A1* | 5/2010 | Kao ...................... B01L 3/5025 506/7 |
| 2010/0267049 | A1* | 10/2010 | Rutter ............... G01N 21/6428 435/7.1 |
| 2012/0183442 | A1* | 7/2012 | Kloepfer ............... G01N 33/92 422/82.05 |
| 2013/0273528 | A1* | 10/2013 | Ehrenkranz ........ G01N 21/8483 435/7.9 |
| 2014/0038202 | A1* | 2/2014 | Wheeler ............ G01N 21/8483 435/7.1 |
| 2014/0072189 | A1 | 3/2014 | Jena et al. |
| 2014/0206956 | A1 | 7/2014 | Rabinovitz et al. |
| 2014/0240491 | A1 | 8/2014 | Kauniskangas et al. |
| 2014/0242612 | A1 | 8/2014 | Wang et al. |
| 2015/0171236 | A1* | 6/2015 | Murray .............. G01N 21/8483 250/208.1 |
| 2015/0308961 | A1* | 10/2015 | Burg ....................... G01N 21/78 |
| 2015/0359458 | A1* | 12/2015 | Erickson .............. A61B 5/1495 382/133 |
| 2016/0077091 | A1* | 3/2016 | Tyrrell ................... G01N 33/94 422/403 |
| 2016/0080548 | A1 | 3/2016 | Erickson et al. |
| 2016/0291010 | A1 | 10/2016 | Kim et al. |
| 2016/0349185 | A1 | 12/2016 | Park et al. |
| 2017/0124690 | A1* | 5/2017 | Sundvor ................ G01N 33/02 |
| 2017/0176418 | A1* | 6/2017 | Bohannon ........ G01N 33/54388 |
| 2017/0184506 | A1* | 6/2017 | Patel ...................... G01N 21/78 |
| 2018/0164222 | A1* | 6/2018 | Pulitzer ........... G01N 33/54388 |
| 2018/0166155 | A1* | 6/2018 | Pulitzer .................. G16H 20/10 |
| 2018/0166171 | A1* | 6/2018 | Pulitzer ............. G01N 21/8483 |
| 2018/0259449 | A1 | 9/2018 | Poulsen et al. |
| 2019/0086296 | A1* | 3/2019 | West .................... G06V 20/695 |
| 2019/0154566 | A1* | 5/2019 | Ast ....................... A61B 5/7225 |
| 2019/0187154 | A1* | 6/2019 | Kumar ............ G01N 33/54388 |
| 2019/0195789 | A1* | 6/2019 | Pan ........................ G01J 3/4338 |
| 2019/0226985 | A1* | 7/2019 | Roberts ............... G01N 21/274 |
| 2019/0343386 | A1* | 11/2019 | Pulitzer .................. G16H 50/20 |
| 2019/0376966 | A1* | 12/2019 | Pulitzer ........... G01N 33/54388 |
| 2020/0003698 | A1* | 1/2020 | Lu ............................ G06V 20/10 |
| 2020/0292539 | A1* | 9/2020 | Ren .................. G01N 33/54388 |
| 2020/0327670 | A1* | 10/2020 | Connor ................. G06T 19/006 |
| 2020/0355613 | A1* | 11/2020 | Hunter ................... G01N 33/53 |
| 2021/0088506 | A1* | 3/2021 | Berg .................... G01N 33/526 |
| 2021/0096083 | A1* | 4/2021 | Klein ......................... G06T 7/80 |
| 2021/0327092 | A1* | 10/2021 | Jiang ..................... B60W 40/02 |
| 2021/0373010 | A1* | 12/2021 | Liu ......................... G01N 21/78 |
| 2022/0238224 | A1* | 7/2022 | Kilgarlin ............... G01N 21/78 |
| 2022/0266248 | A1* | 8/2022 | Qin ....................... B01L 3/5023 |
| 2022/0283155 | A1 | 9/2022 | Cao et al. |
| 2022/0299525 | A1* | 9/2022 | Ozcan ............. G01N 33/54387 |
| 2022/0397576 | A1* | 12/2022 | Ansari ............ G01N 33/57525 |
| 2023/0146924 | A1* | 5/2023 | Kumar .................. G16H 30/40 382/128 |
| 2023/0184689 | A1* | 6/2023 | Berg ..................... G06V 30/41 422/82.05 |
| 2023/0251256 | A1* | 8/2023 | Seit-Nebi .............. G01N 21/78 435/5 |
| 2023/0266232 | A1* | 8/2023 | Schaefer ............... G01N 30/90 382/103 |
| 2023/0314424 | A1* | 10/2023 | Rai .................. G01N 33/54388 435/287.7 |
| 2023/0384293 | A1* | 11/2023 | Canale .................. G01N 33/66 |
| 2024/0302375 | A1* | 9/2024 | Kight .............. G01N 33/57449 |

FOREIGN PATENT DOCUMENTS

| | | |
|---|---|---|
| CN | 104977278 A | 10/2015 |
| CN | 105334320 A | 2/2016 |
| CN | 106370843 A | 2/2017 |
| CN | 106771160 A | 5/2017 |
| CN | 206756844 U | 12/2017 |
| CN | 207751981 U | 8/2018 |
| CN | 108693173 A | 10/2018 |
| CN | 108918860 A | 11/2018 |
| CN | 109061205 A | 12/2018 |
| CN | 109116027 A | 1/2019 |
| CN | 109444423 A | 3/2019 |
| CN | 110231477 A | 9/2019 |
| CN | 110780064 A | 2/2020 |
| EP | 2313787 B1 | 11/2017 |
| WO | 20140045802 A | 4/2014 |
| WO | 2022049436 A1 | 3/2022 |
| WO | 2022049438 A1 | 3/2022 |
| WO | 2022049439 A1 | 3/2022 |
| WO | 2022049440 A1 | 3/2022 |
| WO | 2022049441 A1 | 3/2022 |

OTHER PUBLICATIONS

International Search Report for PCT International Application No. PCT/IB2021/057613, mailed on Dec. 20, 2021, 9 pages.
International Search Report for PCT International Application No. PCT/IB2021/057614, mailed on Nov. 10, 2021, 3 pages.
International Search Report for PCT International Application No. PCT/IB2021/057615, mailed on Nov. 8, 2021, 3 pages.
International Search Report for PCT International Application No. PCT/IB2021/057616, mailed on Dec. 20, 2021, 8 pages.
International Search Report for PCT International Application No. PCT/IB2021/057617, mailed on Nov. 8, 2021, 4 pages.
Lee, "NutriPhone: A Mobile Platform for Low-Cost Point-of-Care Quantification of Vitamin B12 Concentrations", 2016, Scientific Reports, vol. 6, No. 1, 28237, pp. 1-8. XP055850387.
Lee, "Performance Improvement of the One-Dot Lateral Flow Immunoassay for Aflatoxin B1 by Using a Smartphone-Based

(56) References Cited

OTHER PUBLICATIONS

Reading System", 2013, Sensors, vol. 13, No. 4, pp. 5109-5116. XP055145211.

Lu, "Integration of a Lateral Flow Immunoassay Panel for Gastroenteritis with Swab-Based Sample Preparation Cartridge", 2017, Texas State University, 83 pages. XP055728407.

Mudanyali, "Integrated Rapid-Diagnostic-Test Reader Platform on a Cellphone", 2012, Lab on a Chip, vol. 12, No. 15, pp. 2678-2686. XP055058669.

Shuo, "Quantitative Analytical Colloidal Gold Instrument Using Android Smart Phone", 2017, IEEE International Conference on Intelligent Techniques in Control, Optimization and Signal Processing (INCOS), pp. 1-5, XP033325029.

Zhang, "An Integrated, Accurate, Rapid, and Economical Handheld Consumer Gluten Detector", 2019, Food Chemistry, vol. 275, pp. 446-456, XP085515073.

* cited by examiner

1600 identify background regions of output
signal area based on background
fit - to - observed intensity delta — 1602 measure delta at indicator
lines of output signal area — 1604 determine target analyte
concentration based on deltas
measured at indicator lines — 1606

CHROMATOGRAPHIC READER DEVICES FOR BIODETECTION

CROSS-REFERENCE TO RELATED APPLICATIONS

This Application is a national stage filing under 35 U.S.C. § 371 of International Patent Application No. PCT/IB2021/057613, filed 18 Aug. 2021, which claims the benefit of Provisional U.S. Patent Application No. 63/074,825, filed 4 Sep. 2020, the entire disclosure of each of which is incorporated herein by reference.

SUMMARY

This disclosure is directed generally to biodetection, and more specifically, to reader devices configured to perform biodetection. Lateral flow devices (LFDs), paper-based diagnostic test trips, immunochromatographic test strips, and other types of test strips that provide biological chromatographic assays are often used for rapid, on-site diagnostic tests to determine the presence/absence of a variety of analytes related to human health. Examples of analytes that can be detected using biological chromatographic test strips include serologic analytes (e.g., serum antibodies), fertility and pregnancy-associated hormones, allergens, microbes and other infectious disease agents, cancer biomarkers, etc. Biological chromatographic test strips are often relatively small devices that include recognition elements which are conjugated or otherwise paired to a signal-generating tag (i.e., a fluorescent label, colorimetric nanoparticle, a magnetic particle, etc.). The signal-generating tag typically outputs an indication, visible to the unaided eye, of whether the test's target analyte is present at a detectable level in a test sample placed on the biological chromatographic test strip.

This disclosure is directed to reader devices that automate a reading process of biological chromatographic test strips. Existing test strip reading, which is done by eye, is subject to variation in interpretation between different observers. Additionally, the reader devices of this disclosure may enable quantitative biological chromatographic assay result collection, by forming and outputting estimates of target analyte quantity and/or concentration in a given test sample. Reader devices of this disclosure may also enable the collection of potentially valuable metadata. For example, a reader device of this disclosure may incorporate detection systems that execute mapping functions to perform quantitative measurements using one or more features of the biological chromatographic output signal that vary with analyte concentration. Reader devices of this disclosure may include, be coupled to, or activate varying numbers of sensors in different use case scenarios, and may sometimes utilize additional sensors to automate aspects of results generation and/or to integrate metadata with the generated result(s).

The device configurations and techniques of this disclosure provide various technical improvements in the technical field of biodetection devices. Biological chromatographic test strips are being used increasingly for diagnostic tests due their ease of use, portability, relatively quick time-to-result, and other convenience-related factors. The signal-generating tags in a biological chromatographic test strip are usually localized to certain areas of the device membrane, and create visible lines that indicate analyte presence, assay completion, or other results. Determining the presence or absence of result lines on biological chromatographic test strips by eye is subjective, which can lead to misinterpretation when the lines are faint. Even as biological chromatographic test strips are being designed to detect a broader range of analytes, their qualitative and subjective nature continues to limit their wider adoption and limit their impact on interventions and care paradigms. The lack of metadata associated with biological chromatographic test strips is another reason for their limited or slowed adoption.

The reader devices of this disclosure overcome these limitations of existing biological chromatographic assay technology by making result interpretation consistent and agnostic to different visual capabilities and other person-to-person variations among observers. Moreover, the reader devices of this disclosure may leverage features of the biological chromatographic test strip output signals to determine or at least estimate the quantity of the analyte in the submitted test sample. In some examples, the reader devices of this disclosure are configured to extract or infer metadata relating to the test results as well. In some examples, the reader devices may locally implement or may be connected to a repository or database, thereby automating the storage of biological chromatographic assay results for future reference and for the creation of auditable test records. By automating test strip output signal interpretation, the reader devices of this disclosure may also facilitate greater biological chromatographic test strip throughput in labs or similar environments. In some examples, multiple reader devices of this disclosure may form a networked system that collectively reduce the overall time-to-result and improve biological chromatographic test strip-associated workflows by allowing for distributed test locations.

The details of one or more examples of the invention are set forth in the accompanying drawings and the description below. Other features and advantages will be apparent from the description and drawings, and from the claims.

DETAILED DESCRIPTION

In the following detailed description of example embodiments, reference is made to specific example embodiments by way of drawings and illustrations. These examples are described in sufficient detail to enable those skilled in the art to practice what is described, and serve to illustrate how elements of these examples may be applied to various purposes or embodiments. Other embodiments exist, and logical, mechanical, electrical, and other changes may be made.

Features or limitations of various embodiments described herein, however important to the example embodiments in which they are incorporated, do not limit other embodiments, and any reference to the elements, operation, and application of the examples serve only to define these example embodiments. Features or elements shown in various examples described herein can be combined in ways other than shown in the examples, and any such combinations is explicitly contemplated to be within the scope of the examples presented here. The following detailed description does not, therefore, limit the scope of what is claimed.

Figure 1:
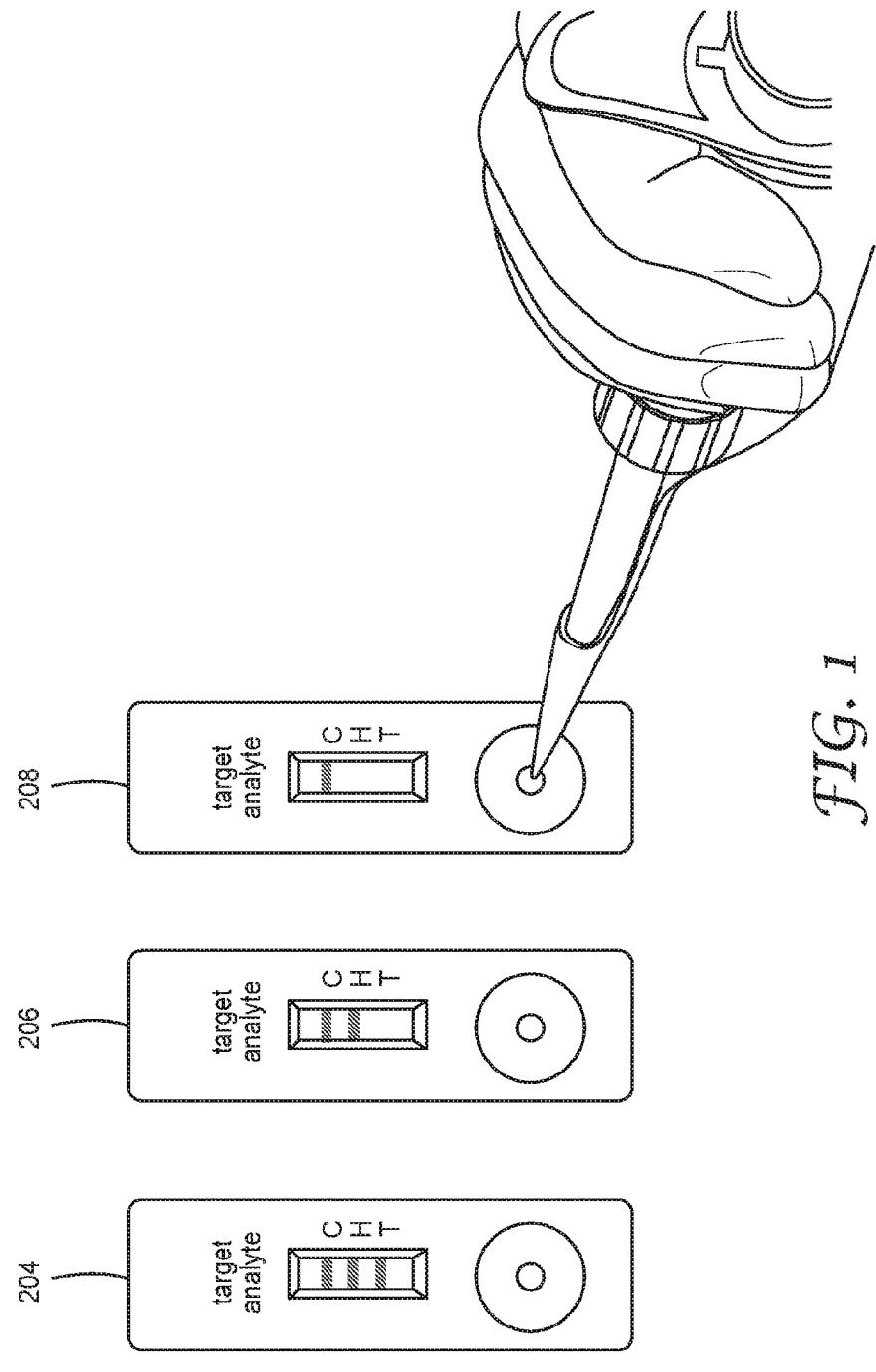
FIG. 1 is a conceptual diagram illustrating different test results as detected by a reader device of this disclosure from various biological chromatographic test strips.

FIG. 1 is a conceptual diagram illustrating different test results as detected by a reader device of this disclosure from various biological chromatographic test strips. FIG. 1 is described in the context of biological chromatographic test strips 204, 206, and 208 representing three instances of similarly constructed test strips. It will be appreciated, however, that the reader devices of this disclosure are compatible with multiple types of biological chromatographic test strips, such as LFDs, immunochromatographic test strips, food safety-related test strips, whether paper-based (cellulose-based), plastic-based, film-based, etc. The respective output signal areas of each of test strips 204-208 include areas for three indicator lines, namely, a control ('C') line, a hook ('H') line, and a test ('T') line. Biological chromatographic test strip 204 is illustrated in a state that indicates a positive test result, while biological chromatographic test strip 206 is illustrated in a state that indicates a negative test result.

The control line shown in the respective output signal areas of biological chromatographic strips 204 and 206 is consistently present in the illustrated use case scenarios. The control line provides a reference sub-image that the reader devices of this disclosure may use to determine the presence/absence and (if present) the intensity of other lines that may appear in the output signal areas depending on the detection of a target analyte in a submitted test sample. The hook line shown in the respective output signal areas of biological chromatographic strips 204 and 206 is a consistently present, based on the respective test samples being of an appropriate concentration to perform analysis with respect to the target analyte.

By detecting the presence of the hook line in both of the use case scenarios illustrated by way of biological chromatographic test strips 204 and 206, the reader devices of this disclosure may determine that the test samples submitted via biological chromatographic test strips 204 and 206 are of appropriate concentrations to determine whether or not the target analyte is present in the respective test sample at a detectable amount (e.g., at at least a threshold concentration). The states of the output signal areas of biological chromatographic test strips 204 and 206 differ in that the test line is present in the case of biological chromatographic test strip 204, while the test line is absent in the case of biological chromatographic test strip 206.

The reader devices of this disclosure may leverage attributes of the detected control line, and optionally, attributes of the detected hook line, to determine the presence of the test line in the case of biological chromatographic test strip 204 and the absence of the test line in the case of biological chromatographic test strip 206. In some examples, the reader devices of this disclosure may also use comparative attributes between respective line pairs formed from the detected control line, the detected hook line, and (in the case of biological chromatographic test strip 204) the detected test line to discern the quantity of the target analyte in the submitted test sample.

In FIG. 1, biological chromatographic test strip 208 is illustrated in a state that indicates that the submitted test sample was invalid in terms of generating a result for testing for the target analyte. As shown in FIG. 1, the output signal area of biometric chromatographic test strip 208 shows the control line as being present, but with the hook line and test line both being absent. In the case of biological chromatographic test strip 208, the reader devices of this disclosure may use color intensities at the expected locations of the hook line and (optionally) the test line to determine the inconclusive result of the test sample submitted via biological chromatographic test strip 208. In accordance with aspects of this disclosure, the reader devices may also use intensity ratios between the control line and hook line, and (optionally) ratios between the intensities of the test line and the control line to determine the absence of the test line. Consistent with other aspects of this disclosure, reader devices of this disclosure (or computing systems coupled thereto) may use other functions of the intensities, such as the ratios described above, or any other functions consistent with the data received.

Based on detecting the absence of the hook line using individual line intensities and relative line intensities in the use case scenario shown by way of biological chromatographic test strip 208, the reader devices of this disclosure may determine that the test sample submitted via biological chromatographic test strip 208 is defective in some way. For example, the reader devices may determine that the submitted test sample is overloaded (e.g., with too much of the target analyte, and should be diluted), is of insufficient quantity (e.g., the test sample was not deposited on biological chromatographic test strip 208 or was deposited in too small of a quantity to be tested for the target analyte), was over-diluted (e.g., with too much water or other diluting agent), or is defective in some other way.

As described in greater detail below, the reader devices of this disclosure may use the individual color intensities of the control line, hook line, and test line, as well as ratios between the color intensities of various pairs of these lines to determine: (i) the presence/absence of a target analyte in the submitted test sample; and (ii) if present, an approximate quantity (e.g., concentration expressed in parts per million) of the target analyte in the submitted test sample. In this way, the reader devices of this disclosure provide one or more technical improvements in the technical field of biodetection. As one example of a technical improvement in the technical field of biodetection, the reader devices of this disclosure may reduce or potentially even eliminate the subjectivity of presence/absence determinations made by inspecting biological chromatographic strips by eye.

A potential data precision improvement provided by the reader devices of this disclosure is the elimination of implicit biases of human test strip readers, such as provider bias, which might skew medical diagnoses and could, coupled with the subjective nature of reading a biological test strip, lead to the under- or over-identification of a particular test result outcome. As another example of a technical improvement in the technical field of biodetection, the reader devices of this disclosure derive and provide data indicating the quantity of the target analyte in the test sample, as opposed to existing technologies that only provide a binary determination of whether a target analyte is present in or absent from the test sample.

Figure 2:
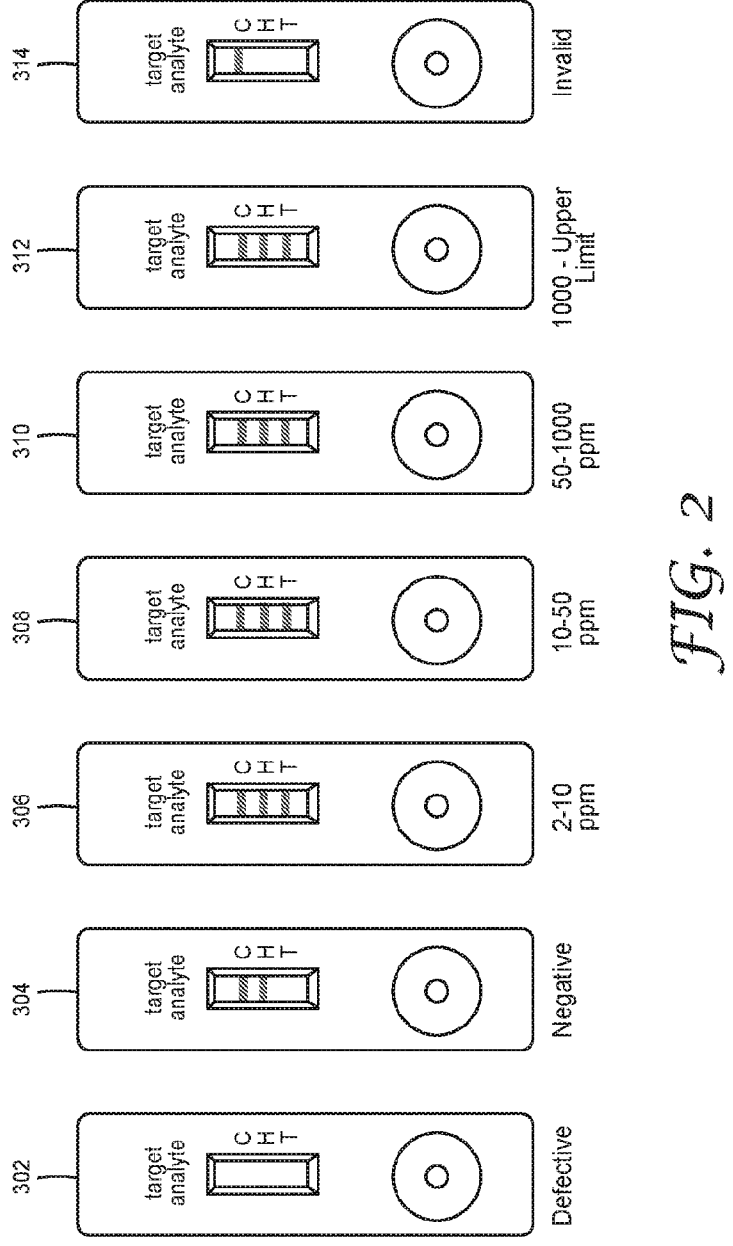
FIG. 2 is a conceptual diagram illustrating different test results detected by a reader device of this disclosure from various biological chromatographic test strips.

FIG. 2 is a conceptual diagram illustrating different test results detected by a reader device of this disclosure from various biological chromatographic test strips. FIG. 2 is described in the context of biological chromatographic test strips 302, 304, 306, 308, 310, 312, and 314, each of which represents an individual instance of various test strips of similar construction. It will be appreciated, however, that the reader devices of this disclosure are compatible with multiple types of biological chromatographic test strips, such as LFDs, immunochromatographic test strips, food safety-related test strips, whether paper-based (cellulose-based), plastic-based, film-based, etc. As in the example of FIG. 1, the respective output signal areas of each of test strips 302-312 include areas for three indicator lines, namely, a control ('C') line, a hook ('H') line, and a test ('T') line.

Biological chromatographic test strip 302 is illustrated in a state that indicates a defective test, biological chromatographic test strip 304 is illustrated in a state that indicates a negative test result, each of biological chromatographic test strips 306-312 is illustrated in a state that indicates a positive test result, and biological chromatographic test strip 314 is illustrated in a state that indicates an invalid (e.g., inconclusive) test result. The invalid test result in the case biological chromatographic test strip 314 may be due to various issues with respect to the submitted test sample, including, but not limited to, the various types of defects described above with respect to biological chromatographic test strip 208 of FIG. 1, such as a target analyte concentration exceeding an upper threshold for generating valid test results. The negative test result in the case biological chromatographic test strip 304 may be due to reasons including, but not limited to, reasons described above with respect to biological chromatographic test strip 206 (e.g., sub-lower threshold concentration of the target analyte) of FIG. 1. The defective state in the case of biological chromatographic test strip 302 may be due to one or more of various factors, such as structural damage to biological chromatographic test strip 302, flow issue caused by solids in the test sample or any other obstructions of capillary action within the working of biological chromatographic test strip 302, chemical or biochemical changes in the conjugate material or the bound chemicals, etc.

In the instances of biological chromatographic test strips 306-312, the reader devices of this disclosure may use the individual color intensities of the respective test lines and the relative color intensities of the respective test lines with one or both of the control and/or hook lines of the same strip to determine a range in which the concentration of the target analyte in the test sample that triggered the positive test result falls. In the case of biological chromatographic test strip 306, the reader devices of this disclosure analyze the individual and relative color intensities of the test line to determine that the target analyte is present in the test sample in a range of two (2) to ten (10) parts per million (ppm).

In the case of biological chromatographic test strip 308, the reader devices of this disclosure analyze the individual and relative color intensities of the test line to determine that the target analyte is present in the test sample in a range often (10) to fifty (50) ppm. In the case of biological chromatographic test strip 310, the reader devices of this disclosure analyze the individual and relative color intensities of the test line to determine that the target analyte is present in the test sample in a range of fifty (50) to one thousand (1,000) ppm. In the case of biological chromatographic test strip 312, the reader devices of this disclosure analyze the individual and relative color intensities of the test line to determine that the target analyte is present in the test sample in a range of over one thousand (1,000) ppm, but within an upper threshold concentration.

To generate the results described above with respect to biological chromatographic test strips 306-312, the reader devices described herein may implement one or more quantitative signal-to-analyte algorithms of this disclosure. The reader devices of this disclosure represent signal-detecting devices configured to detect one or more of colorimetric signals, fluorescent signals, magnetic signals, thermal signals, chemical signals, or other signals output by biodetection test strips that are indicative of the presence or absence. Again, the reader devices of this disclosure leverage various qualities of these signals to discern the quantity (or a range thereof) of the target analyte in the test sample submitted via the biodetection test strip. This disclosure primarily describes examples in which the reader devices use optical (whether visible to the human eye or not) signals, such as colorimetric and/or fluorescent signals.

In various use case scenarios consistent with aspects of this disclosure, the reader devices may be execute a model that is trained or formed using a qualitative or quantitative analyte-associated result manually entered by a user, that is automatically generated, or via a hybrid approach of the two. Irrespective of the approach utilized to obtain the result template, the reader devices of this disclosure may use one or more control or reference area(s) in the output signal area of the biological chromatographic test strips to scale the signal (e.g., lines detected via colorimetric or fluorescence detection based techniques) detected in the output signal area. The reader devices may implement (whether locally or via cloud computing) logic that uses some combination of target analyte indicator signals and/or signals from other control or reference area(s) to define a test result that is invalid.

The logic implemented by the reader devices of this disclosure may execute an algorithm to (or may enable an end-user to) compare the detected result against a qualitative or quantitative reference template or function and perform a calculation. In some examples, the logic implemented by the reader devices may execute a trained model (e.g., an artificial neural network) to draw an inference from signal(s) detected from the output signal areas of biological chromatographic test strips 306-312. In instances in which the reader device incorporates or is coupled to a camera or other optical signal detector for output signal-reading purposes, the logic may use one or more images, one or more red-green-blue (RGB) triplets, or other data representative of an example positive result scale, and/or negative result scale, and/or invalid result scale.

In various embodiments, reader devices of this disclosure may include, be, or be part of an apparatus capable of connecting to or integrating one or more biological chromatographic test strips and to automate the process of reading results from the integrated biological chromatographic test strip(s). The reader devices and configurations thereof as described in this disclosure provide technical improvements in the technical fields of bioassays and biodetection by neutralizing obscurities arising out of inter-observer variation, thereby reducing or eliminating at least one source of potential human error. The reader devices and configurations thereof as described in this disclosure also enable quantitative analyte measurement, as shown by way of biological chromatographic test strips 306-312.

Because biological chromatographic test strips compatible with the reader devices of this disclosure may output fluorescent, colorimetric, or other optical signals (whether discernible to the human eye or not), the reader devices may incorporate or be coupled to signal detector hardware that may include, be, or be part of one or more of camera hardware, photodiode hardware, photocell hardware, luminometer hardware, or any other type of signal detector hardware that provides optical signal detection capabilities consistent with the output signals of the biological chromatographic test strips under analysis. In some examples, the reader devices of this disclosure may be constructed such that one or more of the optical signal detectors are further combined with signal-enhancement hardware, such as a film, and/or hardware filter(s), and/or software filter(s). Each signal detector may be configured as a point or as an area detector acting over some or all of the respective signal output area of a biological chromatographic test strip (e.g., an LFD or LFD cassette/cartridge/case), and each signal detector may be configured to ingest the optical signal output from the biological chromatographic test strip for some or all of the time-to-result window.

Figure 3:
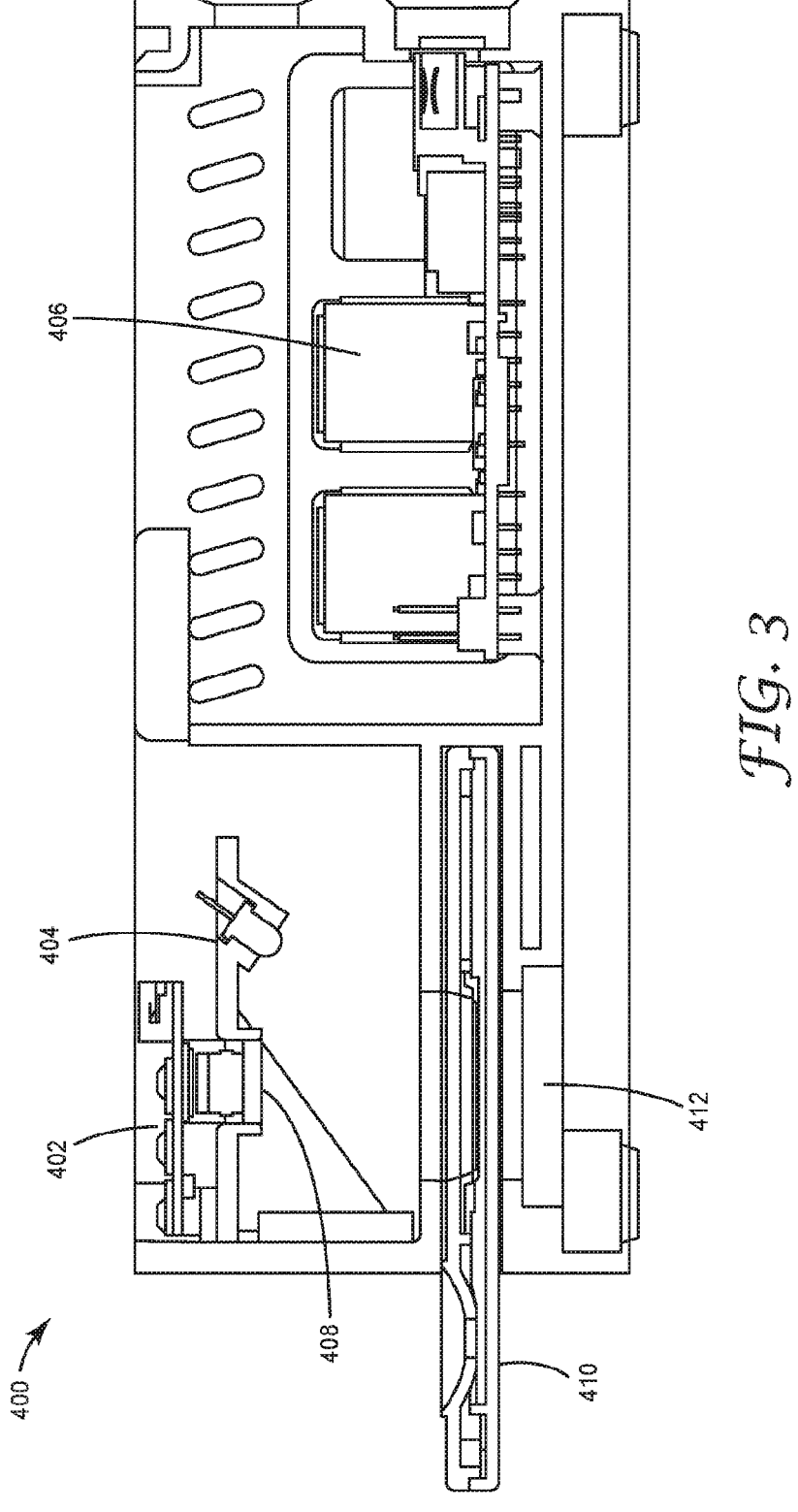
FIG. 3 is a conceptual diagram illustrating a longitudinal cross-section of a reader device of this disclosure.

FIG. 3 is a conceptual diagram illustrating a longitudinal cross-section of a reader device 400 of this disclosure. Reader device 400 represents a dedicated reader that is configured to receive one or more biological chromatographic test strips for individual result analysis. For example, reader device 400 may receive one or more biological chromatographic test strips via dedicated insertion slots. In the particular example of FIG. 3, reader device 400 includes a camera board 402, a light source 404, an on-board computing system 406, a visual filter 408, and a light cavity 412. Reader device 400 is configured to receive a biological chromatographic test strip 410, and may also be configured to receive multiple instances of biological chromatographic test strip 410 over overlapping periods of time.

Camera board 402 may include one or more "primary" signal-detecting devices or units, which may include still camera hardware and/or camera hardware capable of capturing moving pictures (in the case of colorimetric signal detection), and/or photodiode hardware (in the case of fluorescence-based signal detection). In some implementations, camera board 402 may be constructed such that the primary signal-detecting device(s) are supplemented with additional detectors of the same or different type. In some examples, reader device 400 may include one or more components configured to detect supplemental signals including, but not limited to, environmental conditions, result-generation parameters, metadata tags, etc. Examples of environmental conditions include, but are not limited to, ambient temperature (which may be measured by thermometer hardware of reader device 400), humidity (which may be measured by hygrometer hardware of reader device 400), or location (which may be determined using global positioning system (GPS) coordinates obtained using triangulation hardware), etc.

Result-generation parameters include one or more of (but are not limited to) signal-to-noise ratio information (e.g., signal ROI detection), test strip presence recognition, inoculation initiation detection, etc. For example, reader device 400 may determine whether or not biological chromatographic test strip 410 is properly inserted into the slot as part of a test strip presence recognition preprocessing step of the automated biological chromatographic test strip reading processes of this disclosure. Again, biological chromatographic test strip 410 may be paper-based, film-based, may be a cassette or cartridge encasing a stack of paper-based or film-based strips (e.g., an LFD cassette or LFD cartridge), or any other biodetection assay that outputs an optical signal or multiple optical signals. One example of a test-validity parameter for which reader device 400 may assess biological chromatographic test strip 410 is a membrane-to-indicator signal-to-noise ratio (SNR), which reader device 400 may use to detect defective samples, such as an overly concentrated sample deposited on biological chromatographic test strip 410.

Reader device 400 may be configured to evaluate other test-validity parameters in addition to or instead of membrane-to-indicator SNR as well, in various examples in accordance with aspects of this disclosure. In some examples, biological chromatographic test strip 410 may be equipped or supplemented with one or more metatags that provide metadata pertaining to biological chromatographic test strip 410 or to the test sample submitted via biological chromatographic test strip 410. In various examples, biological chromatographic test strip 410 may be equipped with one or more of a near-field communication (NFC) tag, a quick response (QR) code, a barcode, text, icon(s), or information in another machine-readable format. Reader device 400 may invoke camera board 402 and on-board computing system 406 to extract metadata such as information regarding test type, target analyte identification, device lot number, or the like.

In this way, reader device 400 may, in some examples, implement preprocessing steps that improve the data precision and reduce the computing resource footprint with respect to the automated reading process of biological chromatographic test strip 410. As an example of data precision improvement, by checking for the proper insertion (e.g., to correct depth, right-side-up, etc.) of biological chromatographic test strip 410 as a preprocessing step and eliminating scenarios of improper strip insertion or absent strips, reader device 400 eliminates false positives and false negatives that on-board computing system 406 may produce in cases of performing the automated reading process with improperly inserted or absent test strips. As an example of resource footprint reduction, by checking for the proper insertion of biological chromatographic test strip 410 as a preprocessing step and eliminating scenarios of improper strip insertion or absent strips, reader device 400 eliminates instances in which on-board computing device 406 would otherwise perform the automated reading process unnecessarily and in a resource-wasteful way.

In some implementations, on-board computing system 406 may represent a single-board computer that interfaces with camera board 402 and other components of reader device 400. On-board computing system 406 may include a system on a chip (SoC), which represents an integrated circuit (IC) that combines one or more central processing units (CPUs), one or more memory units, input/output (I/O) interfaces or ports, and secondary storage hardware on a single substrate or microchip. In some examples, on-board computing system 406 may combine the SoC with a CPU (e.g., an ARM-compatible CPU) and/or a graphics processing unit (GPU), such as in examples in which on-board computing system 406 represents a Raspberry Pi® single-board computer. In other examples, on-board computing system 406 may represent a multi-board computer. In any event, on-board computing system 406 represents a computing system that can be integrated into reader device 400 without the need for additional peripherals to facilitate the integration.

As such, on-board computing system 406 equips reader device 400 with processing circuitry, which may include programmable processing circuitry and/or fixed-function circuitry, and in various non-limiting examples, may be embodied in one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the terms "processing circuitry" and/or "processor" may refer to any of the foregoing structure or any other structure suitable for implementation of the techniques described. In addition functionalities described with respect to on-board computing system 406 may be provided within dedicated hardware modules and/or dedicated modules of hardware programmed with suitable software. In some examples, the functionalities attributed to on-board computing system 406 may be fully implemented in one or more circuits or logic elements, which are generally described as "processing circuitry" herein.

In various examples, on-board computing system 406 may implement certain functionalities described herein on an integrated circuit (IC) or a set of ICs (e.g., a chip set). In various implementations, on-board computing system 406 may combine various units in a hardware unit or a collection of interoperative hardware units, including one or more processors or units of processing circuitry as described above, in conjunction with suitable software and/or firmware.

Visual filter 408 may include, be, or be part of various types of hardware, materials, or logic configured to block certain wavelengths of light. In some examples, visual filter 408 may include a heat-absorbing filter, such as an infrared (IR) filter that blocks certain IR wavelengths from passing through, while allowing other wavelengths (e.g., visible light) to pass through. In some examples, visual filter 408 may include an ultraviolet (UV) filter that blocks certain UV wavelengths from passing through, while allowing other wavelengths (e.g., visible light) to pass through. In several examples, visual filter 408 represents a film or coating applied to lens hardware of camera board 402 to limit the wavelength band(s) that are allowed to pass through for capture and image analysis. In various implementations, visual filter 408 may be positioned in front of light source 404, may be positioned in front of lens or photodiode hardware of camera board 402, etc. In other words, in various implementations, reader device 400 may be configured to modify the captured image data at the capture intake stage and/or at the input-generation stage.

In examples in which reader device 400 is configured to implement the automated reading processes of this disclosure with respect to fluorescence-based optical signals output by biological chromatographic test strip 410, camera board 402 may be equipped with and may use photodiodes to capture the fluorescence-based optical signal(s). For instance, camera board 402 may include one or more (one-dimensional or two-dimensional) arrays of photodiodes, such that the photodiodes are positioned over the expected location of output signal area of biological chromatographic test strip 410, once biological chromatographic test strip 410 is properly inserted into the receiving slot.

For instance, as a power-saving mechanism, camera board 402 may activate the photodiode array(s) in response to determining that a mechanical pin is engaged by way of biological chromatographic test strip 410 being inserted properly in the receiving slot. Based on the particular part of the output signal area over which each photodiode array is positioned when biological chromatographic test strip 410 is inserted, each photodiode array may be equipped with a particular filter (which may differ across two or more of the photodiode arrays, or may partially or completely match across two or more of the photodiode arrays). Because of the respective filter films/coatings, each photodiode array may configured to filter light based on one of two polarization states, namely, either a bound fluorescent tag or an unbound fluorescent tag.

Depending on the construction of camera board 402, the photodiode arrays are either mounted on a circuit board, or are communicatively coupled to a microcontroller of reader device 400. On-board computing system 406 may measure or calculate the ratio of signal (as expressed by way of electrical current, e.g., in units of milliamps) associated with each polarization state in the input data relayed by each photodiode array. Using these signal ratios, on-board computing system 406 may calculate the analyte concentration (or range band thereof) that caused biological chromatographic test strip 410 to output the fluorescent signal corresponding to a test line.

That is, in the case of available fluorescence at the test line, on-board computing system 406 may use the amount of fluorescence to determine analyte concentration range. Similarly, on-board computing system 406 may use any available fluorescence at the hook line of the output signal area of biological chromatographic test strip 410 to determine test validity. Similarly to the colorimetric examples described above, on-board computing system 406 may use both individual fluorescence values at the expected line locations of the output signal area of biological chromatographic test strip 410, as well as relative fluorescence values between the line locations to determine one or more of test validity, analyte presence, or analyte concentration.

Reader device 400 also includes light source 404. Light source 404 is positioned to function as a spotlight on the output signal area of biological chromatographic test strip 410 upon proper insertion into the receiving slot of reader device 400. Light source 404 may be configured to emit light in visible or non-visible wavelength bands. In various examples, light source 404 may include or represent one or more semiconductor light sources, such as one or more light emitting diodes (LEDs). In LED-based examples, the color of the light emitted by light source can be attenuated using the band gap crossing threshold of the incorporated semiconductor(s). In some implementations, light source 404 is an IR LED, in that light source 404 is configured to emit IR wavelength light. In other implementations, light source 404 may be configured to emit visible light, and in other implementations still, light source 404 may be configured to emit UV light. In any event, light source 404 is configured to illuminate the output signal area of biological chromatographic test strip 410 to aid camera board 402 in capturing data that can be more accurately and efficiently analyzed by on-board computing system 406 for analyte detection and quantification.

In the implementation illustrated in FIG. 3, reader device 400 includes light cavity 412. Light cavity 412 represents an optional feature, and reader device 400 may activate a light source positioned at the distal end of light cavity 412 to backlight the output signal area of biological chromatographic test strip 410. Similar to light source 404, a backlighting light source positioned at the distal end of light cavity 412 may include various types of light-emitting devices, such as LEDs or other types, and may be configured to emit light of various wavelengths, whether in the visible color spectrum or not. When activated, light cavity 412 enables a backlighting light source to accentuate or clarify the output signal area of biological chromatographic test strip 410 to aid camera board 402 in capturing data that can be more accurately and efficiently analyzed by on-board computing system 406 for analyte detection and quantification.

Figure 4:
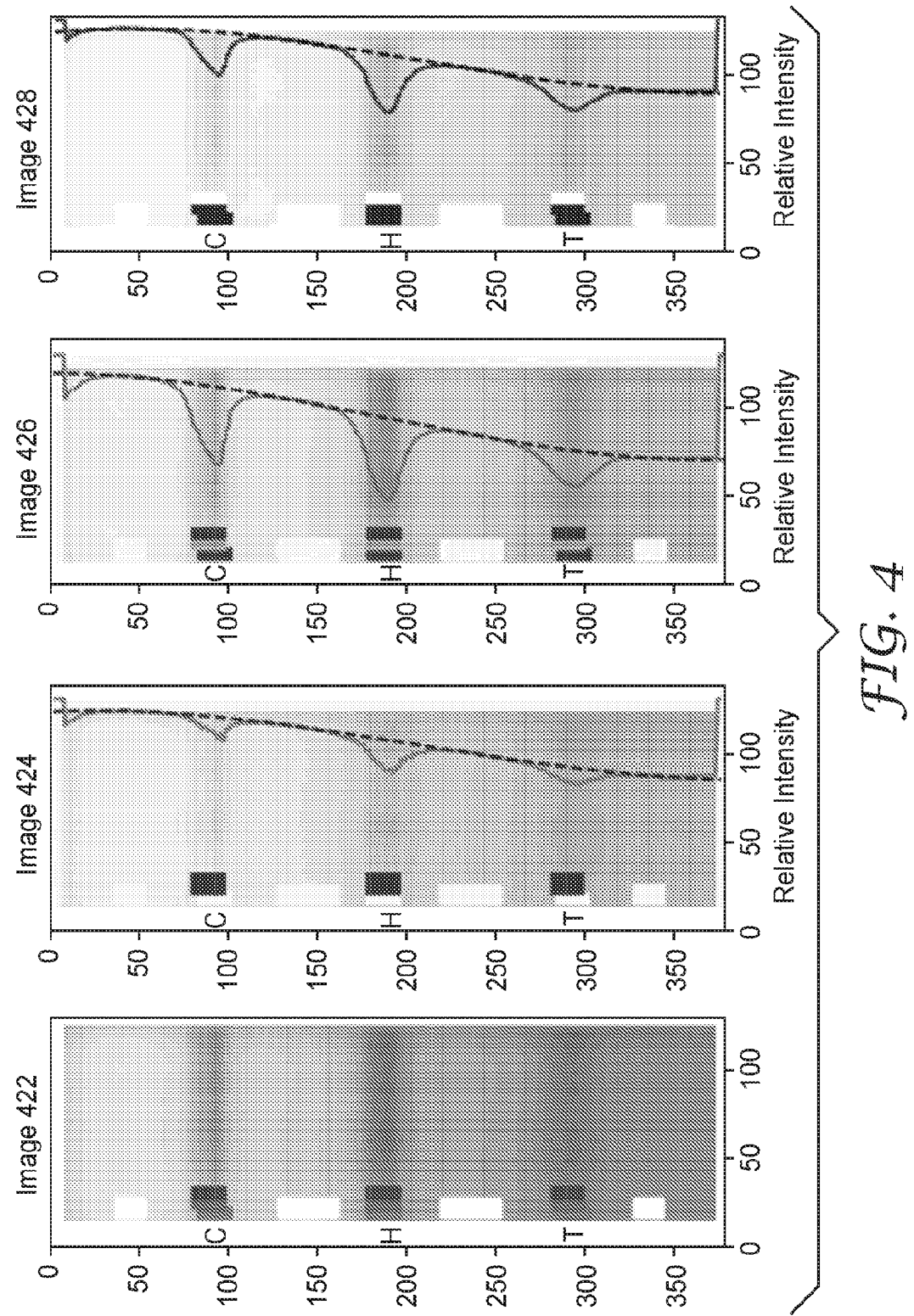
FIG. 4 is a diagram illustrating an example of colorimetric intensity calculation that reader devices of this disclosure may perform as part of the automated test strip reading techniques of this disclosure.

FIG. 4 is a diagram illustrating an example of colorimetric intensity calculation that reader devices of this disclosure may perform as part of the automated test strip reading techniques of this disclosure. The functionalities described with respect to FIG. 4 are described as being performed by on-board computing system 406 of reader device 400 and biological chromatographic test strip 410 of FIG. 3 as a non-limiting example, although it will be appreciated that a variety of devices are compatible with being configured to perform the techniques of this disclosure, including the colorimetric intensity calculations described with respect to FIG. 5.

In accordance with aspects of this disclosure, on-board computing system 406 performs the colorimetric intensity calculations of this disclosure along each respective color channel of the red-green-blue (RGB) color space. 'C', 'H', and 'T' labels are used to denote values pertaining to the control, hook, and test lines respectively. Image 422 illustrates the full color intensities as they are distributed across the output signal area of biological chromatographic test strip 410. The full color intensities are more pronounced along the control, hook, and test lines than they are in the four "background" regions that are formed by these three lines.

On-board computing system 406 is configured to decompose the full color intensities into colorimetric intensities along each of the red, green, and blue color channels of the RGB color space. Image 424 illustrates the colorimetric intensities that on-board computing system 406 obtains in the red color channel, image 426 illustrates the colorimetric intensities that on-board computing system 406 obtains in the green color channel, and image 428 illustrates the colorimetric intensities that on-board computing system 406 obtains in the blue color channel.

On-board computing system 406 may determine a "background fit" that indicates an expected colorimetric intensity for a given color channel in a corresponding background region of the output signal area. In various use case scenarios, on-board computing system 406 may determine the background fit using user input, based on heuristic data, using data obtained from a trained machine learning model, or from any other available source. The dashed line shown in each of images 424-428 tracks the predetermined background fit of the corresponding color channel. The solid line indicates the actual colorimetric intensity observed by on-board computing system 406 from the image data obtained via camera board 402.

As shown in images 424-428, the actual colorimetric intensity for each color channel tracks the background fit closely in the four background regions, but deviates from the background fit at each of the control, hook, and test lines (collectively, the "output lines"). On-board computing system 406 may calculate the respective deltas from the background fit line to the trough of the curve formed by the observed intensity at each of the displayed lines to determine the intensity of each displayed line. In turn, on-board computing system 406 may determine ratios between the test line intensities in each color space to determine the analyte concentration in the test sample submitted via biological chromatographic test strip 410.

For example, on-board computing system 406 may associate particular minima values of a curve in each color space with particular concentration ranges for a given analyte-test strip combination. Based on the observed troughs of the colorimetric intensities fall within an acceptable range of the predetermined minima for each color space, on-board computing system 406 may determine that the analyte concentration is in the corresponding quantity range. In this way, reader device 400 of this disclosure provides technical improvements in this technical field of biodetection assays by providing a granular output (by way of providing a quantity or quantity range) with respect to an analyte that is deemed present, and enhances output accuracy by using relative colorimetric intensities in multiple color channels to generate the result.

Figure 5:
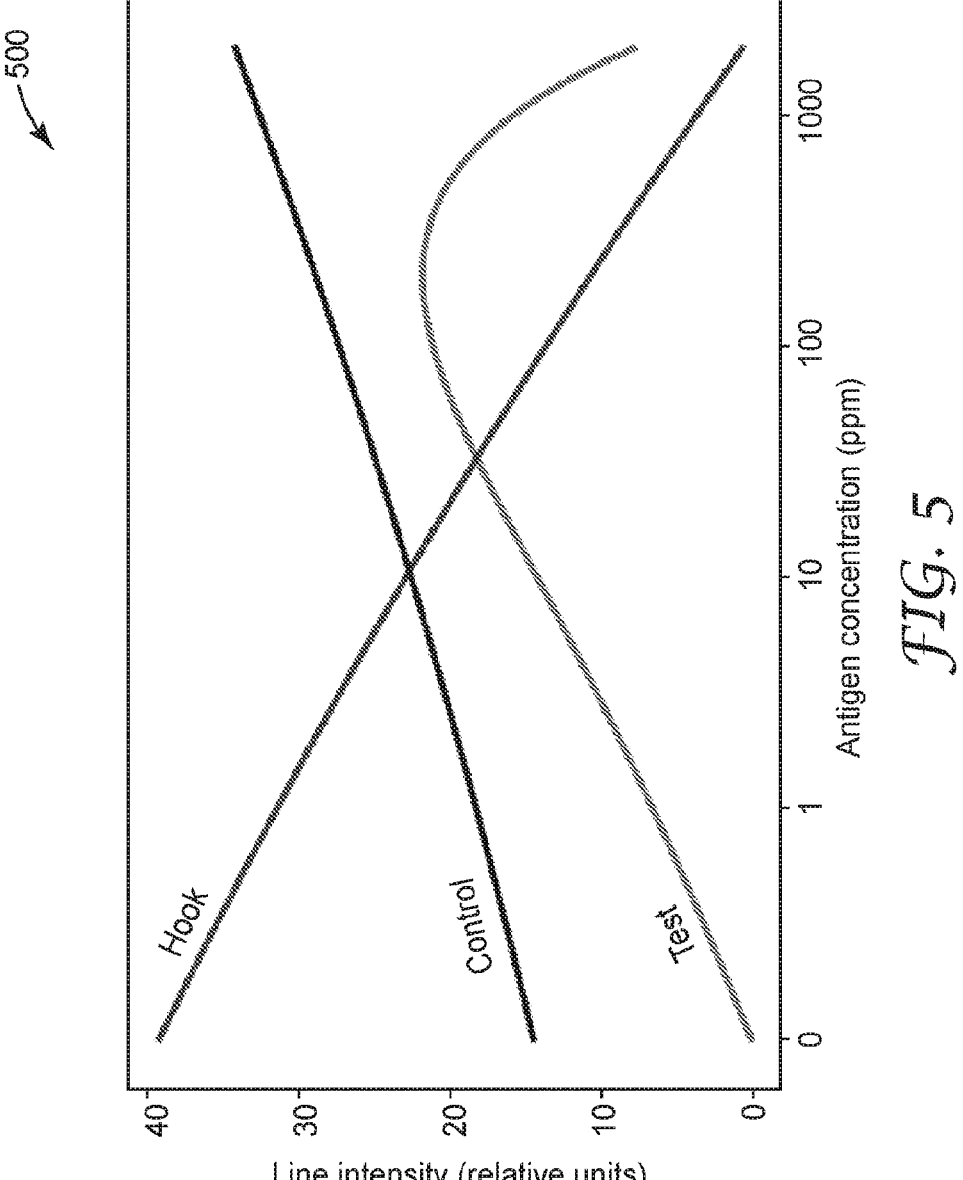
FIG. 5 is a graph illustrating colorimetric intensity variance of control, hook, and test lines displayed via the output signal area of the biological chromatographic test strip of FIG. 4 with corresponding variation in target analyte concentration in the test sample submitted via the biological chromatographic test strip.

FIG. 5 is a graph 500 illustrating colorimetric intensity variance of the control, hook, and test lines displayed via the output signal area of biological chromatographic test strip 410 with corresponding variation in target analyte concentration in the test sample submitted via biological chromatographic test strip 410. Graph 500 is associated with an example of immunochromatographic testing. For instance, in the example of FIG. 5, biological chromatographic test strip 410 may be configured to detect a pathogen (e.g., a virus, such as the influenza virus, coronavirus strains associated with COVID-19, etc.) by detecting one or more antigens that are customarily present on the outside of the target pathogen. Graph 500 may be described in some cases as a semi-quantitative representation of the test result shown in FIG. 2, which shows that features of the lines follow a trend depending on analyte concentration in the submitted test sample.

The horizontal (x-) axis of graph 500 plots the concentration of the antigen being tested for in units of parts per million (ppm). The vertical (y-) axis plots line intensity in relative units. The relative units may express one or more components of colorimetric intensity, such as one or more of luminance values, chromaticity values, etc. Graph 500 may apply to one or more of the RGB color channels for which on-board computing system 402 evaluates the image data received from camera board 402.

As shown in FIG. 5, the colorimetric intensity of the control line is roughly proportional to the antigen concentration, in that the colorimetric intensity of the control line increases with increasing antigen concentration. The colorimetric intensity of the hook line is approximately inversely proportional to the antigen concentration, in that the colorimetric intensity of the hook line decreases with increasing antigen concentration. The colorimetric intensity of the test line varies with the antigen concentration in a manner that generally resembles a non-monotonic distribution.

The individual plot lines shown in graph 500 represent the individual colorimetric intensities of the control, hook, and test lines. In accordance with aspects of this disclosure, on-board computing system 406 may evaluate the ratios between respective pairs of plots along these lines to determine the fit of the observed line intensities with respect to target analyte concentrations known to produce line intensities in a given range. While FIG. 5 illustrates an immunochromatographic test as an example, it will be appreciated that reader device 400 may also implement the techniques of this disclosure with respect to other types of tests, such as enzymatic assays (e.g., to test for horseradish peroxidase as the target analyte), proteomic assays, allergen assays, fusion proteins engineered to react with certain targets (e.g. fusion proteins that react with a nuclear protein of the COVID-19 coronavirus strains), and others.

Figure 6:
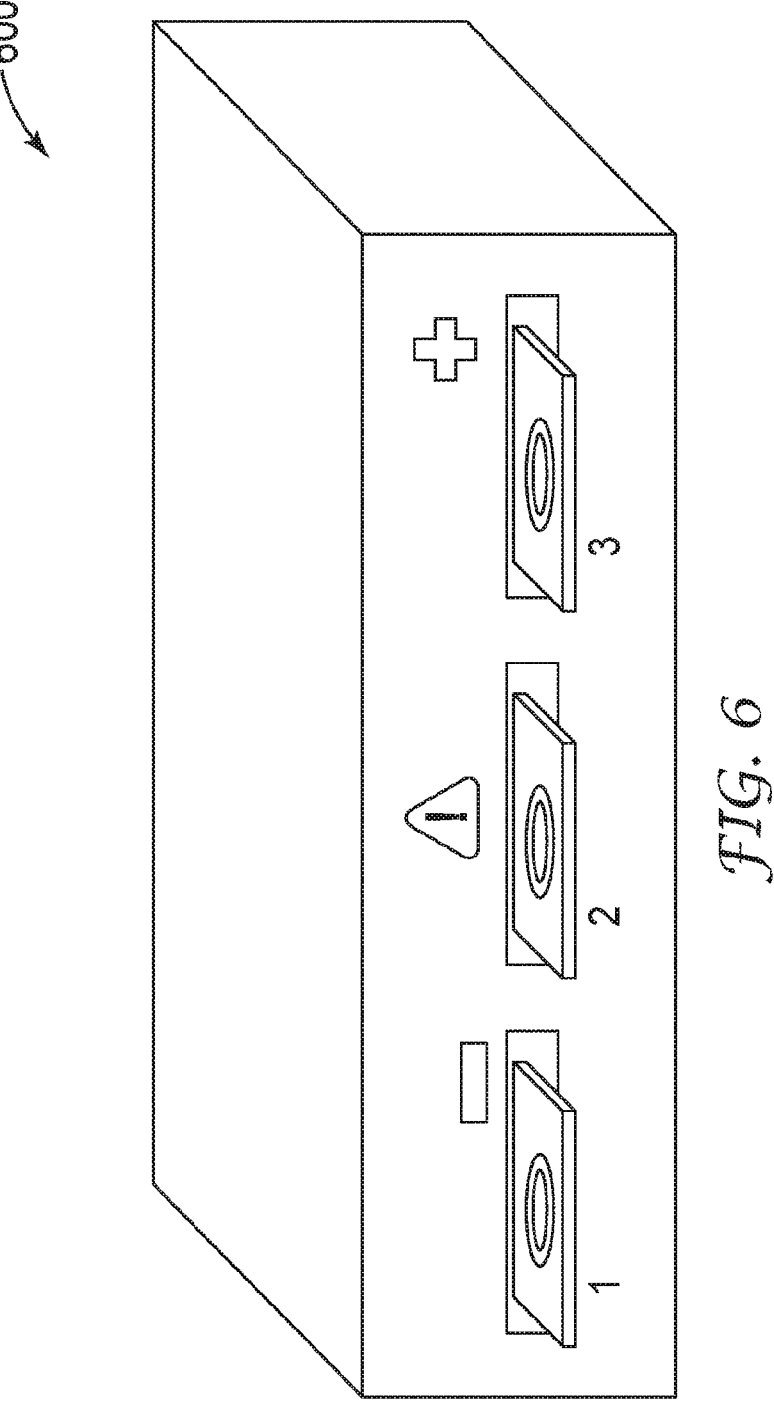
FIG. 6 is a conceptual diagram that illustrates a data-consuming human-machine interface (HMI) of this disclosure.

FIG. 6 is a conceptual diagram that illustrates a data-consuming human-machine interface (HMI) of this disclosure. HMI 600 of FIG. 6, in various examples, may include, be, or be part of reader device 400 of FIG. 3. HMI 600 outputs qualitative results in the illustrated example. In the use case scenario shown in FIG. 6, the biological chromatographic test strip at the left produces a negative result, the biological chromatographic test strip positioned in the middle produces an invalid result (e.g., due to defects in sample submission, strip insertion, etc.), and the biological chromatographic test strip at the right produces a positive result. The negative result indicates that the target analyte is not present in the test sample at a discernible level, while the positive test result indicates that the target analyte was detected in the test sample. HMI 600 may also interface with or represent a data management devices or a data management service host for processing automated readouts of biological chromatographic test results. In cases of HMI 600 interfacing with a remote (e.g., cloud-based) system, HMI 600 enables remote monitoring of analyte detection as well as data centralization for subsequent data and analysis thereof, and/or generation of audit-ready data.

Figure 7:
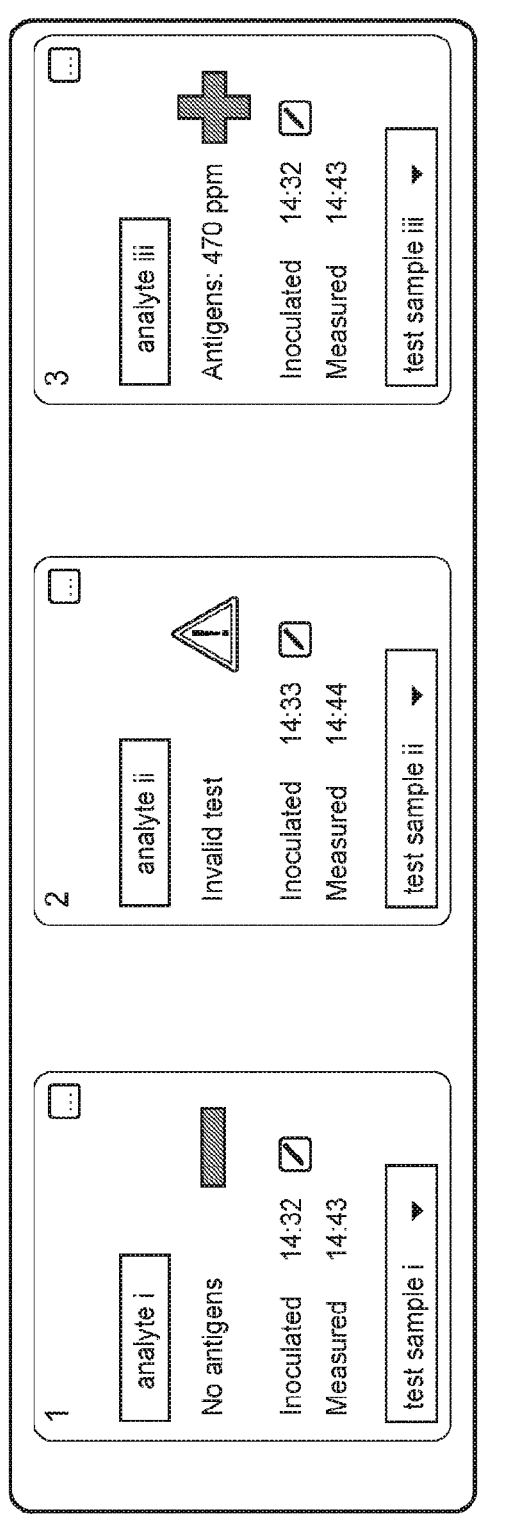
FIG. 7 is a conceptual diagram that illustrates a user interface (UI) that the HMI of FIG. 6 or another user-facing device coupled to the HMI of FIG. 6 may output to inform users of the test results of the biological chromatographic test strips shown in FIG. 6.

FIG. 7 is a conceptual diagram that illustrates a user interface (UI) 700 that HMI 600 or another user-facing device coupled to HMI 600 may output to inform users of the test results of the biological chromatographic test strips shown in FIG. 6. UI 700 is an interactive UI in that UI 700 represents a sample data-entry and consumption dashboard. FIG. 7 shows target analyte quantification functionalities of this disclosure. In the case of the negative test result, HMI 600 outputs, via UI 700, a "no antigens" to indicate a zero or indetectable quantity of the target analyte in the test sample. In the case of the positive test result, HMI 600 outputs, via UI 700, a concentration (expressed in units of ppm) of the target analyte in the test sample submitted via the biological chromatographic test strip. In this way, HMI 600 implements techniques of this disclosure to determine a concentration (or a range thereof) of the target analyte in the submitted test sample by implementing image analysis techniques of this disclosure to the output signal areas of individual biological chromatographic test strips.

Figure 8:
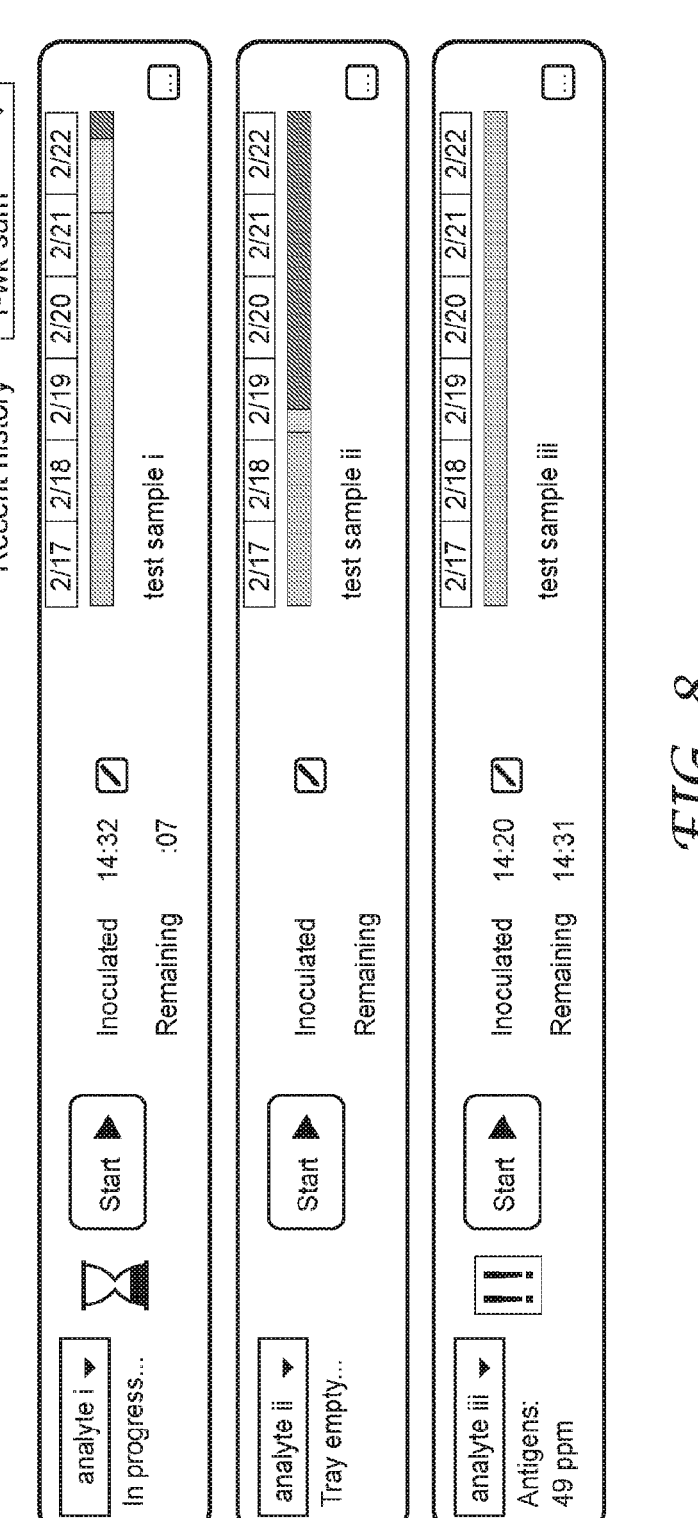
FIG. 8 is a conceptual diagram that illustrates a UI that the HMI of FIG. 6 or another user-facing device coupled to the HMI of FIG. 6 may output to inform users of the test results of the biological chromatographic test strips shown in FIG. 6.

FIG. 8 is a conceptual diagram that illustrates a user interface (UI) 800 that HMI 600 or another user-facing device coupled to HMI 600 may output to inform users of the test results of the biological chromatographic test strips shown in FIG. 6. UI 800 is an interactive UI similar to UI 700 of FIG. 7, but also provides sample data-control capabilities in addition to a sample data-entry and consumption dashboard. FIG. 7 shows target analyte quantification functionalities of this disclosure. HMI 600 outputs, via UI 800, historical data read for each target analyte. In the example of FIG. 8, HMI 600 outputs a one-week sum of the readings. The time period may be attenuated based on user input, or based on different configurations of HMI 600 in different use case scenarios.

Various implementations of this disclosure incorporate the use of one or more data management devices. Data management devices consistent with this disclosure may include or otherwise make use of one or more of local data storage, cloud computing resources, network drives, or any combination(s) thereof. The systems of this disclosure may implement data transfer to and/or from the data management device using various types of wired and/or wireless connections, including, but not limited to, near-field communication (NFC), universal serial bus (USB), Wi-Fi®, Bluetooth®, Ethernet®, combinations thereof, or various. The data management device(s) of this disclosure may provide auto-sync capabilities, or may sync if triggered by user input provided via HMI 600, dashboards such as those shown in UIs 700 and 800, or other application programming interface (API). The interface with one or more instances of reader device 400 may include, but is not limited to, manual-triggering of signal-detection activities and may be on HMI 600, via a dashboard provided by UI 700 or 800, or any other suitable mechanism.

As shown in the example of FIG. 8, the data management device(s) may auto-populate metadata such as upload/download time. Other example of metadata that the data management device(s) of this disclosure may auto-populate may include the origination source, location thereof, etc. The data management device(s) may provide one or more entry and data-consumption feature in the form of HMI(s), dashboards, mobile device application alerts, etc. The data-entry features may include documentation of meta-data relevant to previously read test samples or test samples being read currently, such as target analyte, physical location of sample collection, user ID, test strip lot number, etc.

The data management device(s) of this disclosure may provide the data-entry (and optionally, data consumption) functionalities via HMI 600 or a remote dashboard, such as the dashboards provided by way of UIs 700 and 800. As shown in FIGS. 7 and 8, data-consumption features provided by the data management device(s) of this disclosure may include qualitative and/or quantitative test results, historical data trends, and/or or the results of analytics performed on the collected data. In some examples, data-consumption features of this disclosure may also include providing indicators of test validity and/or suggested remediation/mitigation action(s).

Figure 9:
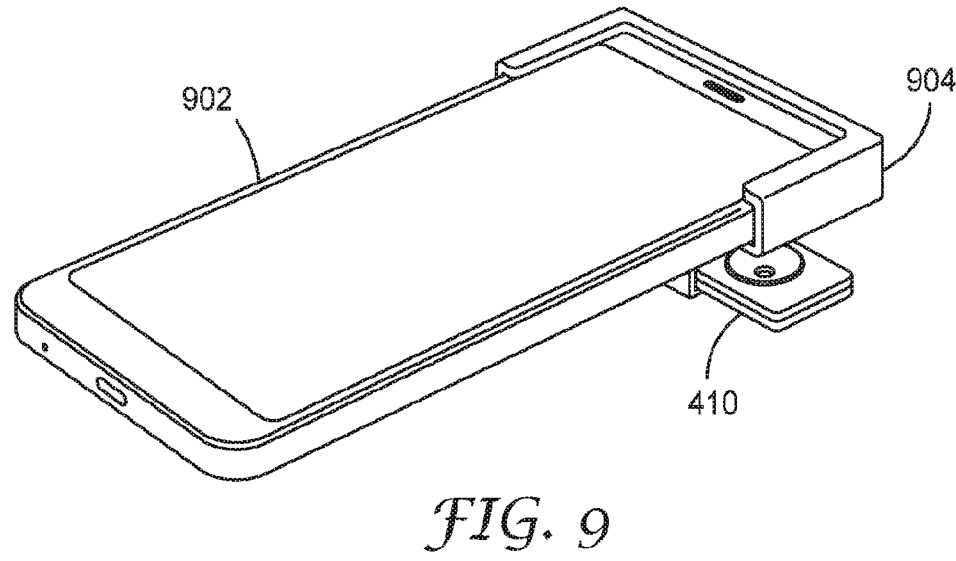
FIGS. 9 and 10 illustrate examples in which the automated biological chromatographic test strip reading functionalities of this disclosure are incorporated into a mobile computing device.
Figure 10:
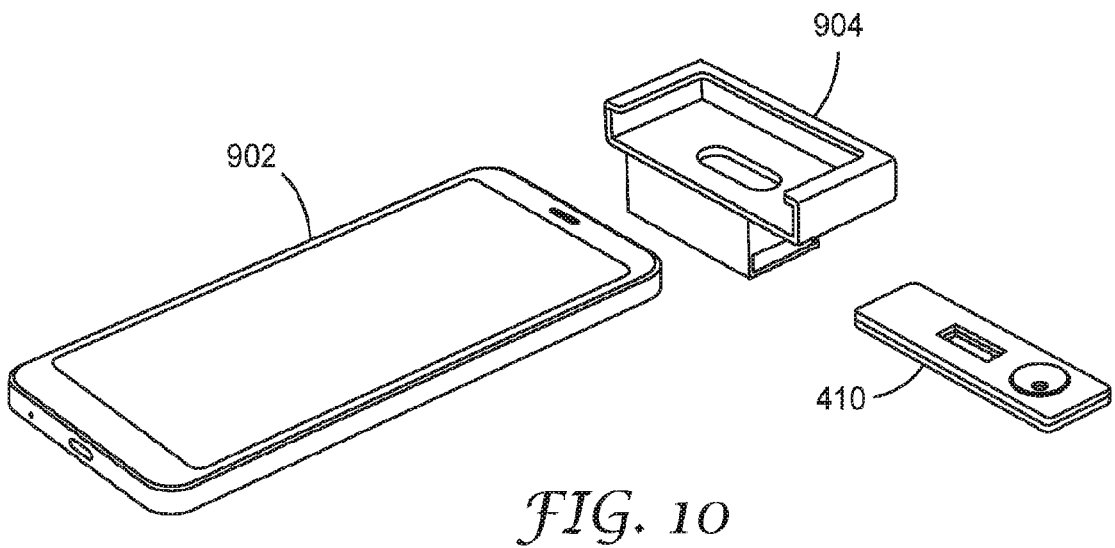

FIGS. 9 and 10 illustrate examples in which the automated biological chromatographic test strip reading functionalities of this disclosure are incorporated into a mobile computing device. In the particular example of FIGS. 9 and 10, smartphone 902 is configured to implement the automated biological chromatographic test strip reading functionalities of this disclosure. In other examples, other types of computing devices may be configured to implement the automated biological chromatographic test strip reading functionalities of this disclosure, such as tablet computers, personal digital assistants (PDAs), smart watches, smart glasses, other types of wearable devices, laptop computers, so-called "netbook" computers, etc.

In the example of FIG. 9, smartphone 902 is configured to perform the automated test strip reading techniques of this disclosure with the aid of a lightbox 904. Lightbox 904 represents a device designed to accentuate or normalize contrast of the output signal area of biological chromatographic test strip 410 to enhance image capture by camera hardware of smartphone 902. For example, lightbox 904 may block light "pollution" from light sources external to smartphone 902 and lightbox 904, thereby limiting the illumination of the output signal area biological chromatographic test strip 410 to light sourced by smartphone 902 and/or lightbox 904.

As shown in FIG. 9, lightbox 904 is equipped with a slot into which biological chromatographic test strip 410 may be inserted. In one example, lightbox 904 may limit the illumination of the output signal area of biological chromatographic test strip 410 to spotlighting provided by a flash LED (or other flash light source) positioned near the lens hardware of rear-facing camera infrastructure of smartphone 904. In another example, lightbox 904 may provide backlighting of the output signal area of biological chromatographic test strip 410 in a way similar to the light cavity-aided backlighting functionalities described above with respect to FIG. 4.

In another example, lightbox 904 may be equipped with a reflective inner surface that reflects the flash source to provide backlighting to the output signal area of biological chromatographic test strip 410. In various examples, lightbox 904 may combine two or more of the lighting-related functionalities described above. While shown in FIG. 9 as being constructed to aid smartphone 902 in capturing image data using a rear-facing camera as an example, it will be appreciated that, in other examples, lightbox 904 may be constructed to aid smartphone 902 in capturing image data using a front-facing camera or other image capture hardware.

FIG. 10 shows an exploded view of FIG. 9. As described with respect to FIG. 10, smartphone 902 may be configured to perform the automated test strip reading techniques of this disclosure without the aid of lightbox 904, in accordance with various aspects of this disclosure. In the example of FIG. 10, smartphone 902 may capture image data representing the output signal area of biological chromatographic test strip 410 using rear-facing camera hardware, front-facing camera hardware, or any other image capture hardware. Smartphone 902 may be configured to capture the image data at varying distances, pre-process the image data to normalize for various external idiosyncrasies, and may perform image processing to determine qualitative and/or quantitative aspects of the test for the target analyte.

In the examples shown in FIGS. 9 and 10, smartphone 902 may be configured to perform one or more of the image processing techniques described above with respect to FIGS. 4 and 5. For example, smartphone 902 may evaluate the individual colorimetric intensities of the control, hook, and test lines displayed in the output signal area of biological chromatographic test strip 410 to determine qualitative, and in some examples, quantitative information associated with the target analyte in the test sample submitted via biological chromatographic test strip 410.

Figure 11:
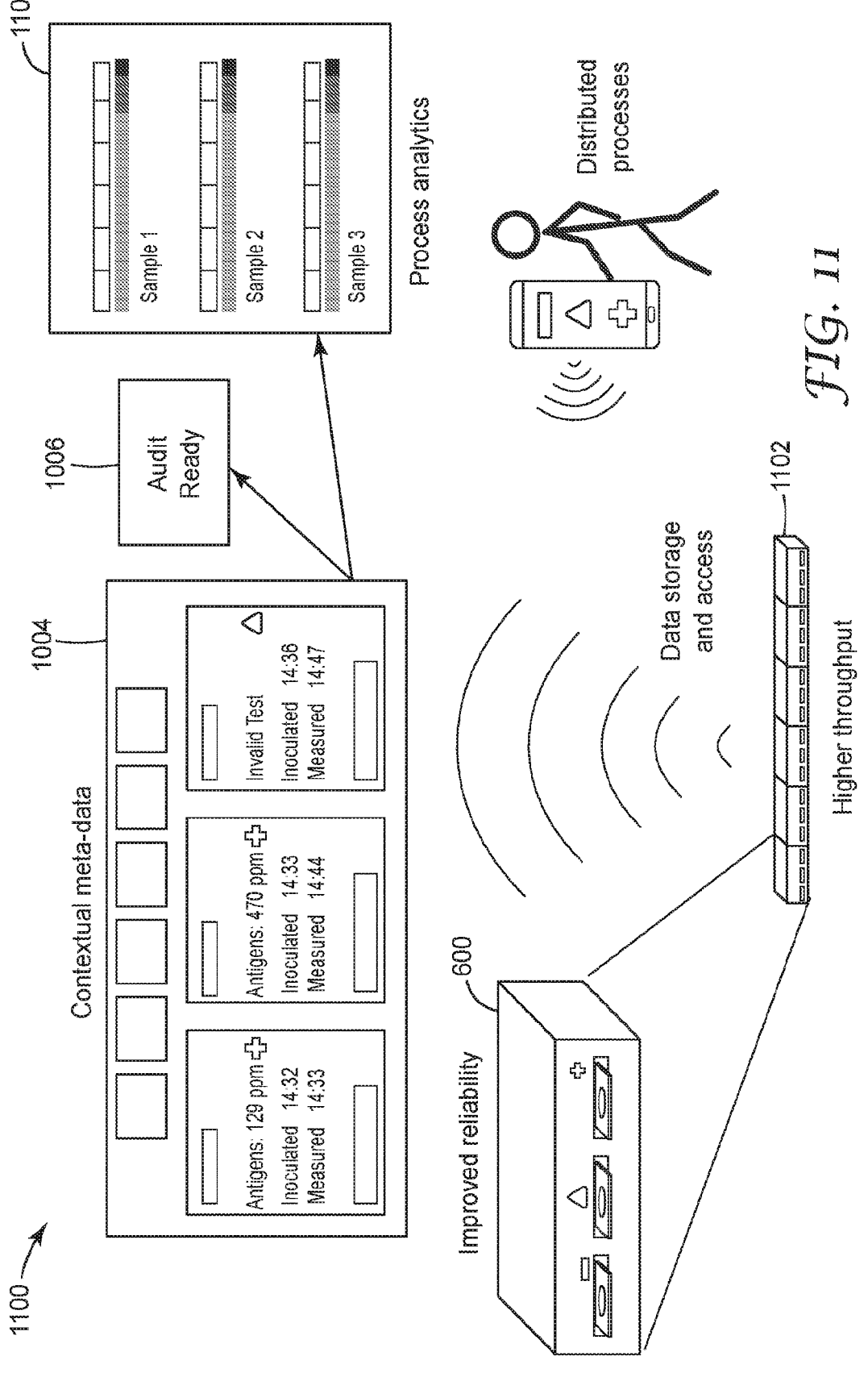
FIG. 11 illustrates an automated workflow for analyte testing and data processing in accordance with aspects of this disclosure.

FIG. 11 illustrates an automated workflow for analyte testing and data processing in accordance with aspects of this disclosure. In the example of system 1100, multiple instances of HMI 600 are integrated to form HMI array 1102. HMI array 1102 may be deployed at a single location or spread across different locations in various examples. HMI array 1102 combines resources of multiple instances of HMI 600 to provide greater throughput in terms of analyte test data collection and cataloging. HMI array 1102 may upload data in a continuous manner or in a batched manner to form contextual metadata 1004, which may be stored to any one or more of the data management devices or systems described above.

In turn, the data management devices/systems of this disclosure may format contextual metadata 1004 to enable users or other systems to extract audit ready data 1006 and/or process analytics 1108. System 1100 may be particularly useful in instances of requiring rapid upscaling of data collection and processing, such as in cases of outbreaks/epidemics/pandemics (e.g., COVID-19 or other infectious diseases), widespread food contamination (e.g., with common allergens), etc. The automated reading techniques of this disclosure, when implemented in a distributed system such as system 110 with the use of contextual metadata 1004, may potentially enable early detection of outbreaks in a community indicated by various factors, such as the number of positive test results, the percentage of tests returned positive, and/or the average analyte load per sample for a given population.

Figure 12A:
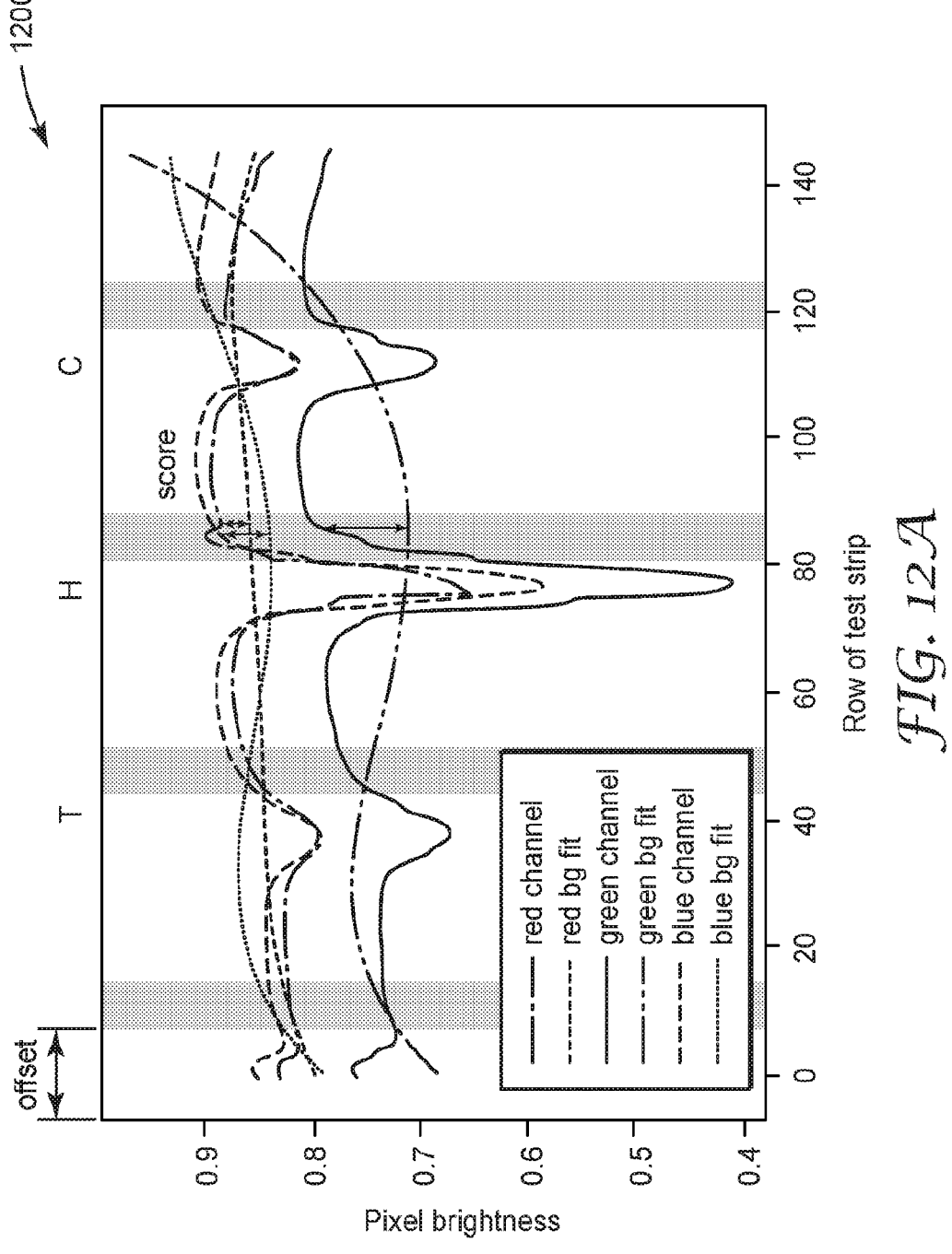
FIGS. 12A & 12B illustrate graphs that show aspects of the automated reading processes that reader devices and/or mobile computing devices may be configured to perform in accordance with aspects of this disclosure.
Figure 12B:
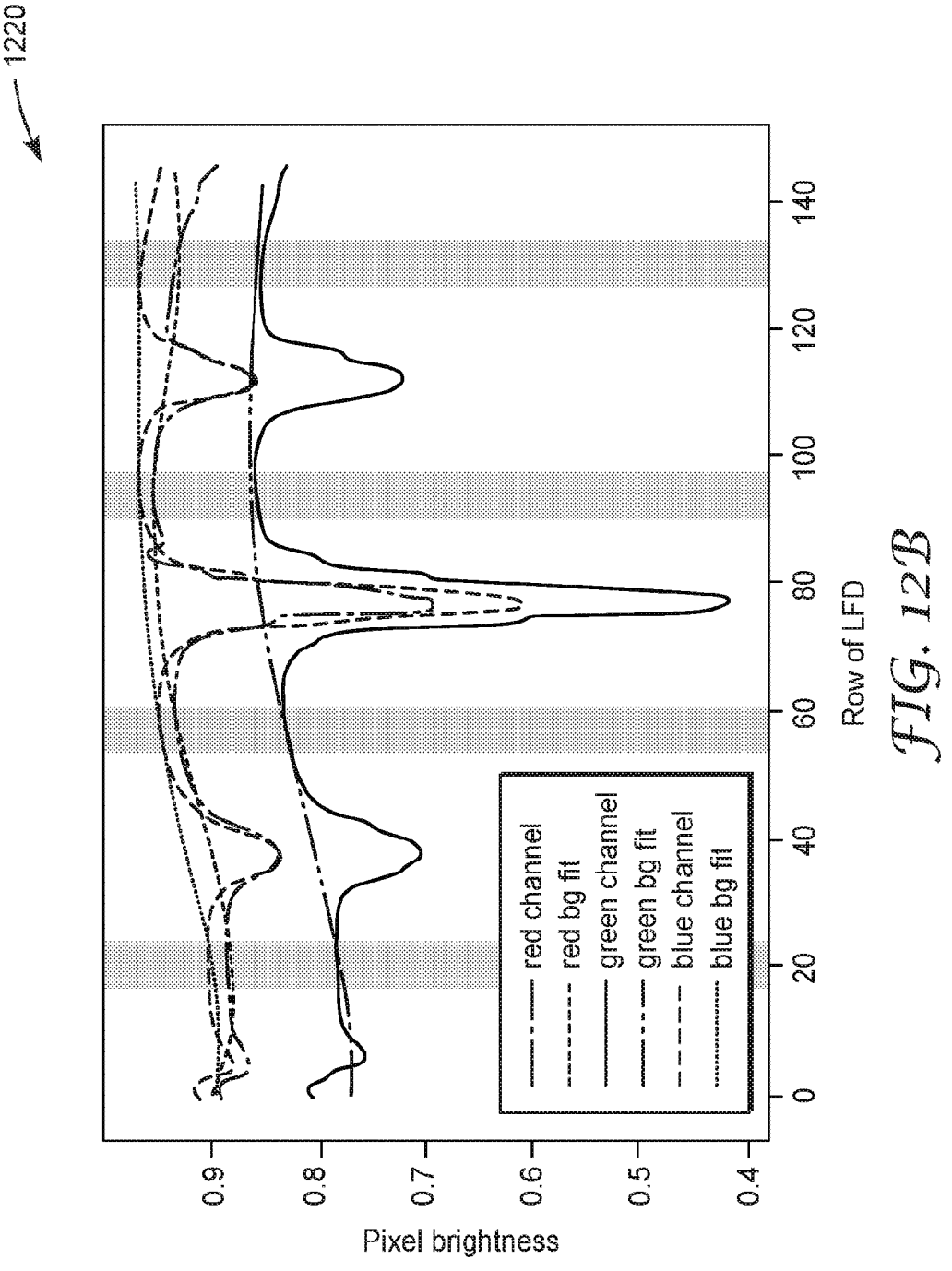

FIGS. 12A & 12B illustrate graphs 1200 and 1220 that show aspects of the automated reading processes that reader device 400 or smartphone 902 may perform in accordance with aspects of this disclosure. Graphs 1200 and 1220 illustrate aspects of individual colorimetric intensity and relative colorimetric intensity evaluations that reader device 400 or smartphone 902 may perform to provide qualitative and/or quantitative results with respect to a target analyte in a test sample submitted via biological chromatographic test strip 410. Reader device 400 and/or smartphone 902 may automate the detection of one or more of the test, hook, or control zones of the output signal area of biological chromatographic test strip using the techniques described herein with respect to FIGS. 12A & 12B.

Reader device 400 or smartphone 902 may use techniques illustrated by way of graphs 1200 and 1220 to perform automated detection of the control, hook, and test zones of the output signal area of biological chromatographic test strip 410, in accordance with aspects of this disclosure. In various examples, reader device 400 or smartphone 902 may preprocess the captured image data in one or more ways, such as by checking for complete insertion of biological chromatographic test strip 410 in the receiver slot of reader device 400 or lightbox 902, checking for adequately stationary placement of biological chromatographic test strip 410 in non-lightbox-based implementations using smartphone 902, etc. Other examples of preprocessing that reader device 400 or smartphone 902 may perform in accordance with aspects of this disclosure include adjusting for the test paper background or test film background, adjusting for the background for the test solution if the solution is not colorless and transparent, adjusting for blemishes in the readable surface (e.g., denting caused by fingernails), etc.

In the case of graphs 1200 and 1220, reader device 400 or smartphone 902 may check the captured image data for a possible three lines of colorimetric deltas. Reader device 400 or smartphone 902 may scan the captured image data for background regions, of which there are four (separated by the three lines), provided that all three of the test, hook, and control lines are. Reader device 400 or smartphone 902 may fit the detected luminance values for each color channel of the RGB color space across the captured image of the output signal area to these background regions. With the possible exceptions of variation due to fluid overspill or lighting geometry idiosyncrasies, the background regions generally adhere (at least approximately if not exactly) to the same colorimetric intensities. Reader device 400 or smartphone 902 may move the four background fit regions across the captured image of the output signal area of biological chromate graphic test strip 410 until the best available fit is detected or until encountering a sufficient offset from the top of the image where the background regions produce the best fit for the color channel under investigation (e.g., as produced by nitrocellulose or other material used).

Graph 1200 illustrates an unsuccessful background fit, as shown by the deviations (labeled as "scores") from the background fit lines to the actual detected intensities in the background regions. In contrast, graph 1220 shows a successful fit, as shown by the closeness or even coincidence of the background fit lines with respect to the actual detected intensities in the background regions. Upon detecting the best available fit in this manner, the dashed background fit lines plotted in graph 1220 are relatively close to their true brightness values in the respective RGB color channels in the background regions of the output signal area of biological chromatographic test strip 410. Reader device 400 or smartphone 902 may examine gaps between these regions to search for signals corresponding to any of the three lines listed above. In the test line window, the offset shown by the depths of the troughs of the true channel brightness in comparison to the background fit brightness provide the colorimetric intensity of the test line. Reader device 400 or smartphone 902 may use a similar trough-based offset calculation to detect the hook line and/or the test line, provided that these signals are detectable from the test.

In the example of graph 1220, the difference between the brightness (or luminance) at the hook line (which is 0.4) and the brightness of the background fit region (which is 0.77)

yields a 0.37 brightness delta for the hook brightness in the green channel Reader device 400 or smartphone 902 may add the brightness delta detected in the green channel for the hook line to the red channel brightness delta and blue channel brightness delta at the hook line location to obtain the overall colorimetric brightness delta for the hook line. Reader device 400 or smartphone 902 may implement similar processing to detect the control and test lines in a first pass by deriving offset values.

In the particular use case scenario shown in graph 1220, the hook line shows significantly greater colorimetric intensity than the control line or the test line, as shown by the deeper troughs of the hook line vis-à-vis the control and test lines in corresponding color channels. Reader device 400 or smartphone 902 may reflect the curve across the x-axis to obtain a residual, and subtract the background fit (dashed) line in the corresponding color channel from the trough of the observed intensity to determine the initial location of the lines. In turn, reader device 400 or smartphone 902 may perform a thorough sweep with windows of pixels that are at the expected width from the manufactured geometry of the test strip.

In examples in which biological chromatographic test strip 410 is an LFD, antibodies lay down in a thickness of approximately one twentieth (1/20th) of the nitrocellulose strip of the LFD. On-board computing system 406 or computing logic of smartphone 902 may pass a window over the captured image of the output signal area of biological chromatographic test strip 410 and search for a window of a size that is 1/20th of the lateral distance the image in which the difference between the true brightness and the background fit are the greatest. If needed, on-board computing system 406 or computing logic of smartphone 902 may can shift the luminance values in a given color channel based on LED brightness.

By implementing these techniques of this disclosure, reader device 400 and smartphone 902 provide the advantage of enabling detection of a given line's absence in cases in which not all three lines are present in a use case scenario. That is, because reader device 400 and smartphone 902 are configured according to aspects of this disclosure to have information indicating where each line is expected to be positioned (or at least an approximation thereof). In cases in which reader device 400 or smartphone 902 detect both the control line and hook line, reader device 400 or smartphone 902 can derive information on the expected location and brightness (in each color channel) of the test line.

While techniques of this disclosure are described above within the closed universe of a single color channel of the RGB color space for ease of discussion, it will be appreciated that reader device 400 and smartphone 902 may implement the image analysis aspects described above in an aggregated way. For instance, on-board computing system 406 and computing logic of smartphone 902 may discern color change in each color channel, and sum the differences to obtain a full-color delta. In an example in which on-board computing system 406 or computing logic of smartphone 902 detect a color change of 20% in the red channel, 30% in the green channel, and 20% in the blue channel, reader device 400 or smartphone 902 may calculate a 70% (or 0.7) sum with respect to the overall color change for a line.

In detecting color change, reader device 400 or smartphone 902 may use a median pixel value over the output signal area (or "indicator region") in a cropped image of biological chromatographic test strip 410. For instance, reader device 400 or smartphone 902 may use the median RGB values (keeping the color channels distinct) in each column of pixels of the cropped image, after detecting and disregarding any blemishes or imperfections (e.g., fingernail damage). Based on the orientation shown in FIG. 12, the techniques are described as being implemented with respect to "columns" due to parallel orientation with respect to the control, hook, and test lines, although in a different orientation, the techniques may be described as being performed with respect to "rows" of pixels.

On-board computing system 406 or computing logic of smartphone 902 may use uncompressed images of the output signal area of biological chromatographic test strip 410 to implement the techniques described above. In some implementations, reader device 400 and/or smartphone 902 may be configured to measure and average values extracted from multiple images taken over a period of time. In this way, reader device 400 and smartphone 902 may be configured according to this disclosure to improve data precision by reducing noise and eliminating randomly occurring outlier data.

That is, reader device 400 and/or smartphone 902 may use a series or multiple series of captured images instead of a snapshot, which tends to represent a timeframe of ⅟₁₅th of a second. In some examples, reader device 400 and/or smartphone 902 may average values for images taken at regular intervals or sporadic intervals over a period of twenty (20) seconds to discern colorimetric intensity transitions. In some examples, reader device 400 and/or smartphone 902 may use multiple series of captured images, such as multiple twenty (20)-second series over five (5) minutes or fifteen (15) minutes to detect colorimetric intensity transitions. In these implementations, reader device 400 and/or smartphone 902 produce positive results earlier than the ending of the image series time window, if a sufficient colorimetric intensity transition is detected for the test line. The time from the start of the image analysis to the generation of a positive result is referred to as a "time to result window" or an "inoculation period" herein.

Because spotlighting and/or backlighting may vary due to environmental factors or other reasons, reader device 400 and/or smartphone 902 may apply filtering, whether on the light-providing side or on the image capture side. In this way reader device 400 and/or smartphone 902 may normalize for environmental conditions or customize the lighting to suit the particular appearance or composition of biological chromatographic test strip 410 for better image capture. The "scores" illustrated in FIG. 12 represent background fit-to-actual intensity variations produced by plot differentials on graph 1220. In general, by implementing the techniques described with respect to FIG. 12, reader device 400 and/or smartphone 902 may, in accordance with aspects of this disclosure, improve low-end sensitivity, and may compensate for variations in manufacturer or manufacture specifications of biological chromatographic test strip 410 and/or for variations in insertion characteristics with respect to biological chromatographic test strip 410.

Figure 13A:
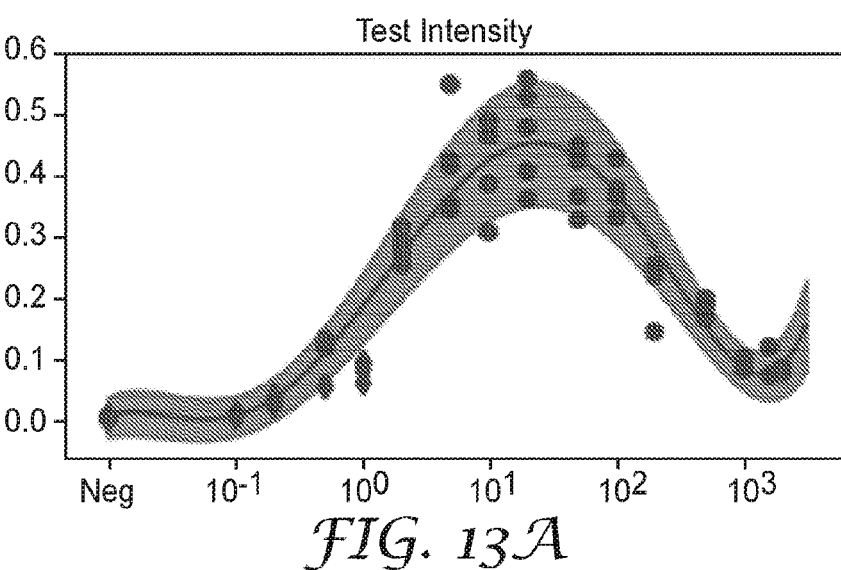
FIGS. 13A-13C are graphs that illustrate the individual colorimetric intensities of the control, hook, and test lines displayed via the output signal area of the biological chromatographic test strip of FIG. 4, with analyte concentration-correlated variance.
Figure 13B:
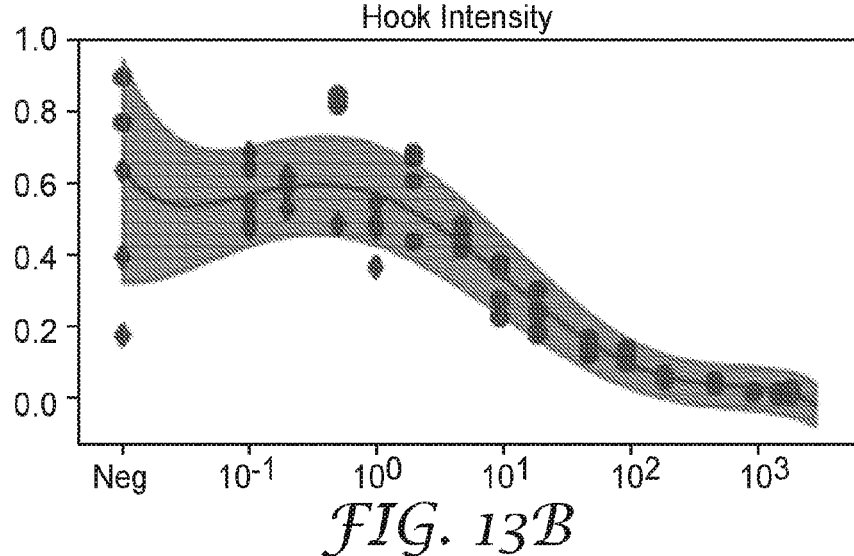
Figure 13C:
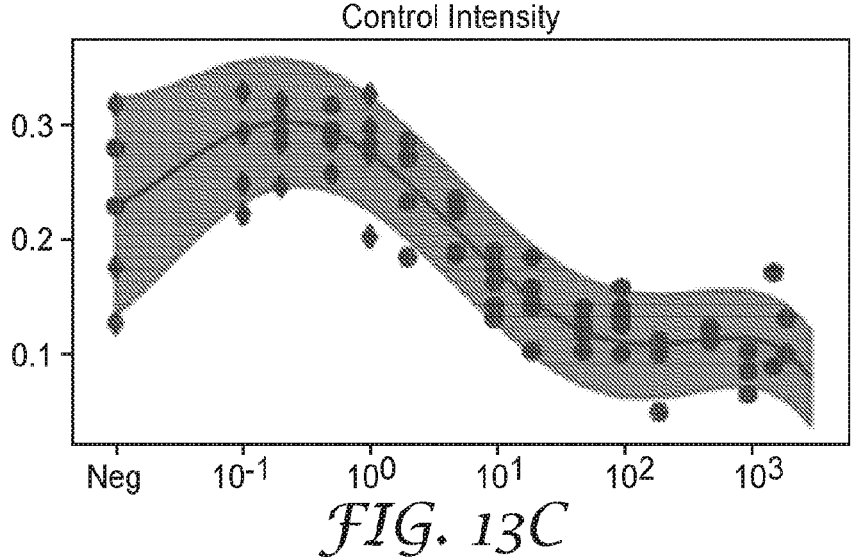
Figure 13D:
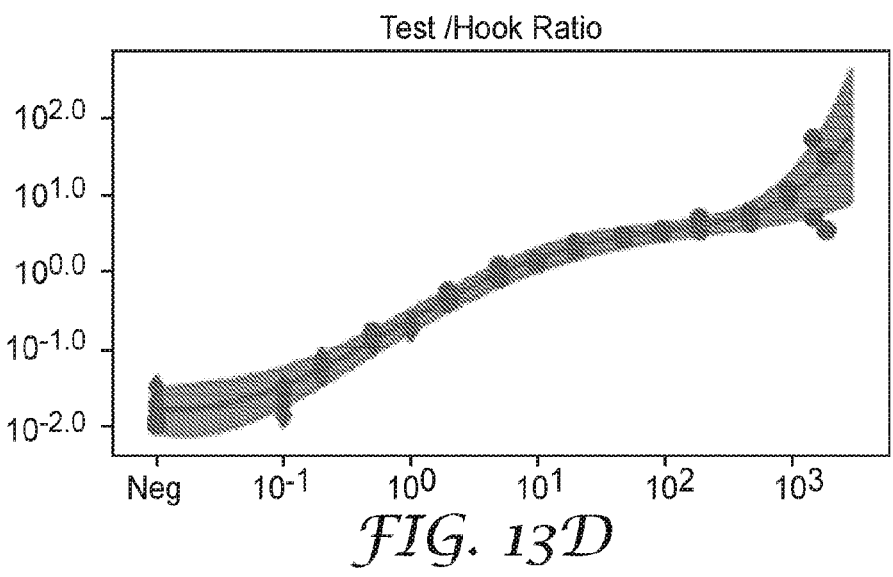
FIGS. 13D-13F are graphs illustrating relative intensities shown as ratios between respective pairs of the individual colorimetric intensity plots of FIGS. 13A-13C, also with analyte concentration-correlated variance.
Figure 13E:
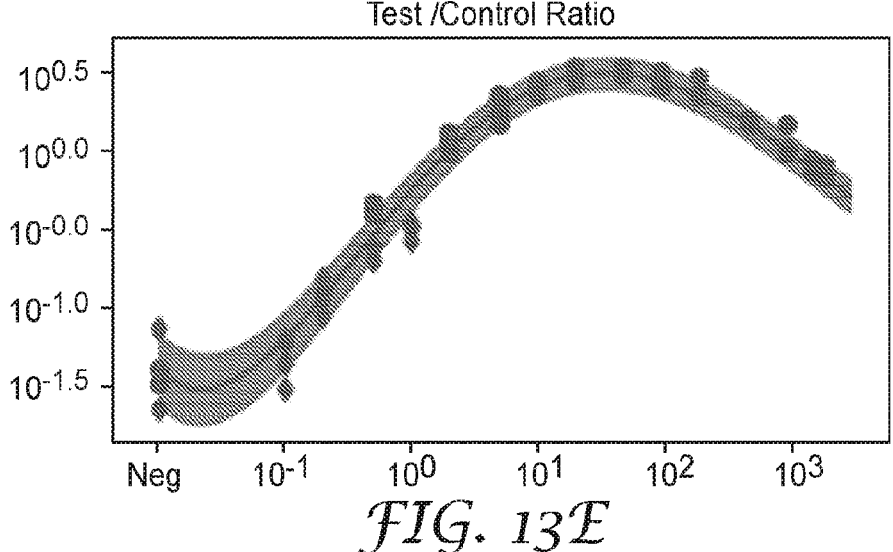
Figure 13F:
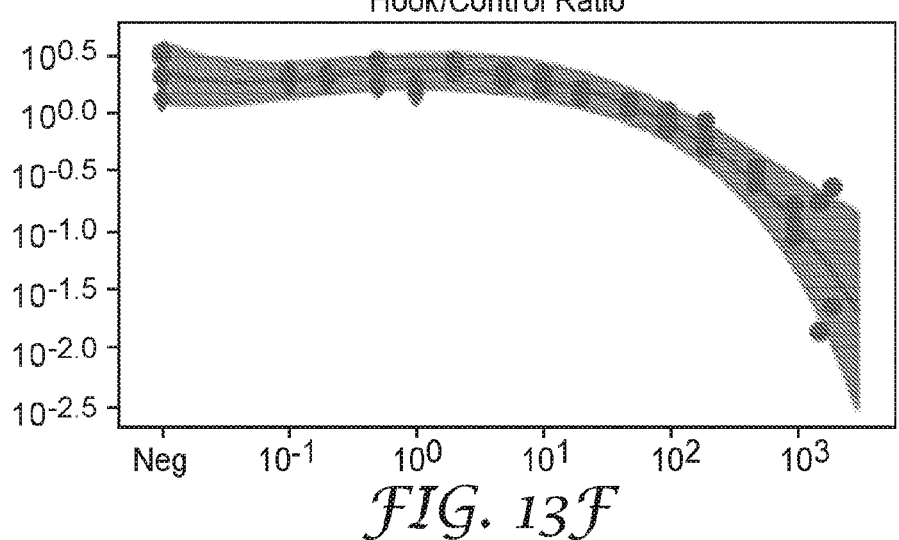

FIGS. 13A-13C are graphs that illustrate the individual colorimetric intensities of the control, hook, and test lines displayed via the output signal area of biological chromatographic test strip 410, with analyte concentration-correlated variance. FIGS. 13D-13F are graphs illustrating relative intensities shown as ratios between respective pairs of the individual colorimetric intensity plots of FIGS. 13A-13C, also with analyte concentration-correlated variance. Reader device 400 and smartphone 902 may implement the techniques of this disclosure to output qualitative and quantitative target analyte results by leveraging all of the illustrated indicator lines' colorimetric intensities as well as the ratios between the colorimetric intensities of respective pairs of the illustrated indicator lines. FIG. 5 discussed above may also be described as a simplified version of a combination of any one or more of the graphs of FIGS. 13A-13F.

Figure 14:
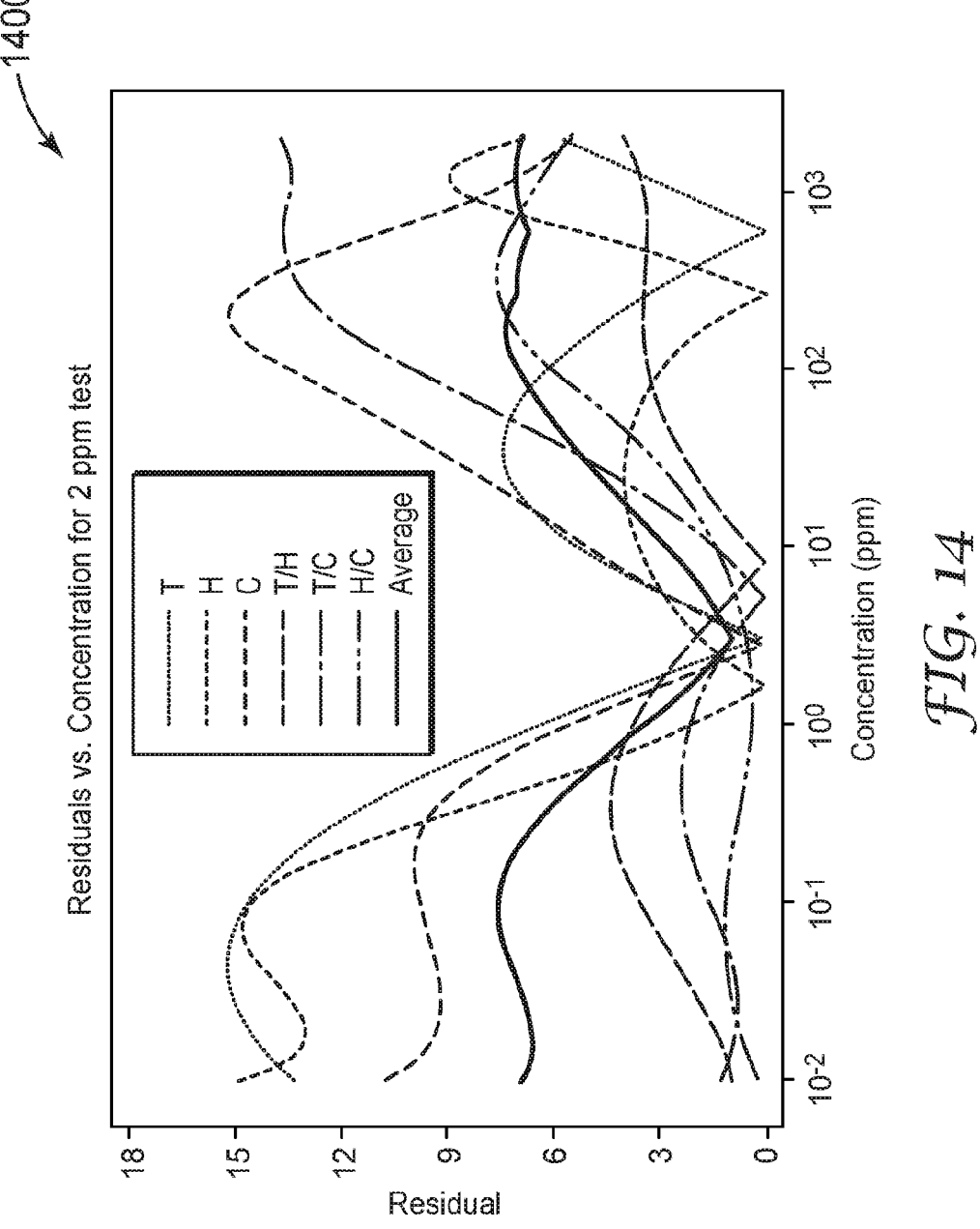
FIG. 14 illustrates a graph that shows the colorimetric intensity residuals as they vary with analyte concentration.

FIG. 14 illustrates graph 1400 that shows the colorimetric intensity residuals as they vary with analyte concentration. Graph 1400 shows the variation of each individual indicator line's colorimetric intensity residuals, as well as the residuals between respective pairs of these indicator lines. The solid line shows the average (e.g., mean, median, or mode) of all of the plots. The plot lines in graph 1400 illustrate aggregate intensity deltas across all three color channels in the RGB color space. The x-axis plots target analyte concentration values ranging from zero (0) ppm to two thousand (2000) ppm. Graph 1400 shows three line intensities of a single test and three line intensity ratios relative to that particular line's or ratio's respective solid curve shown in FIGS. 13A-13F. As such, graph 1400 relates to a single test in which reader device 400 or smartphone 902 checks that particular test against a model (e.g. the collection of data shown in FIGS. 13A-13F) to find that particular test's most accurate or closest concentration estimate.

The colorimetric intensity residuals corresponding to each indicator line pair (between an observed and a trained model) changes based on the analyte concentration, as shown by the variation in the y-coordinates corresponding to shifts along the x-axis. Reader device 400 and smartphone 902 may leverage the colorimetric intensity shift for each line with analyte concentration to perform the analyte quantification techniques of this disclosure. Graph 1400 shows a trend in line colorimetric intensity residuals and also a trend in the variance between the lines' colorimetric intensity residuals. Reader device 400 and/or smartphone 902 may generate the most probable analyte concentration that would produce the particular set of intensities and intensity variations given by a trained model (e.g. as trained using data from FIG. 13) from a single test sample.

In some examples, devices of this disclosure may train a model (e.g., linear regression, neural network, etc.) on a sufficient set of analyte-related and colorimetric intensity-related data, and load the trained model to reader 400 and/or smartphone 902 (and/or a cloud-connected system) for the execution phase. The solid-line "average" curve represents the sum of all of the various dashed-line curves, with each of the dashed-line curves representing the probabilities of the colorimetric intensities (or ratios derived therefrom) being produced by a particular concentration of the target analyte under examination. Graph 1400 is an example in which reader device 400 or smartphone 902 may analyze results of a test of unknown concentration to generate a 2 ppm estimate via the estimation processes described herein. In this particular example, the minima of the "average" curve represents the most likely spot at which the average colorimetric intensity value coincides with a 2 ppm concentration, and with the respective minimas of the remaining cures representing the most likely points at which the individual colorimetric intensity (or intensity variation, as the case may be) produced the intensity/variation. As such, the quantification techniques of this disclosure use all three intensities and all three ratios, with a less accurate trained model if any individual intensity or variation used in the training or execution input is excluded.

Figure 15:
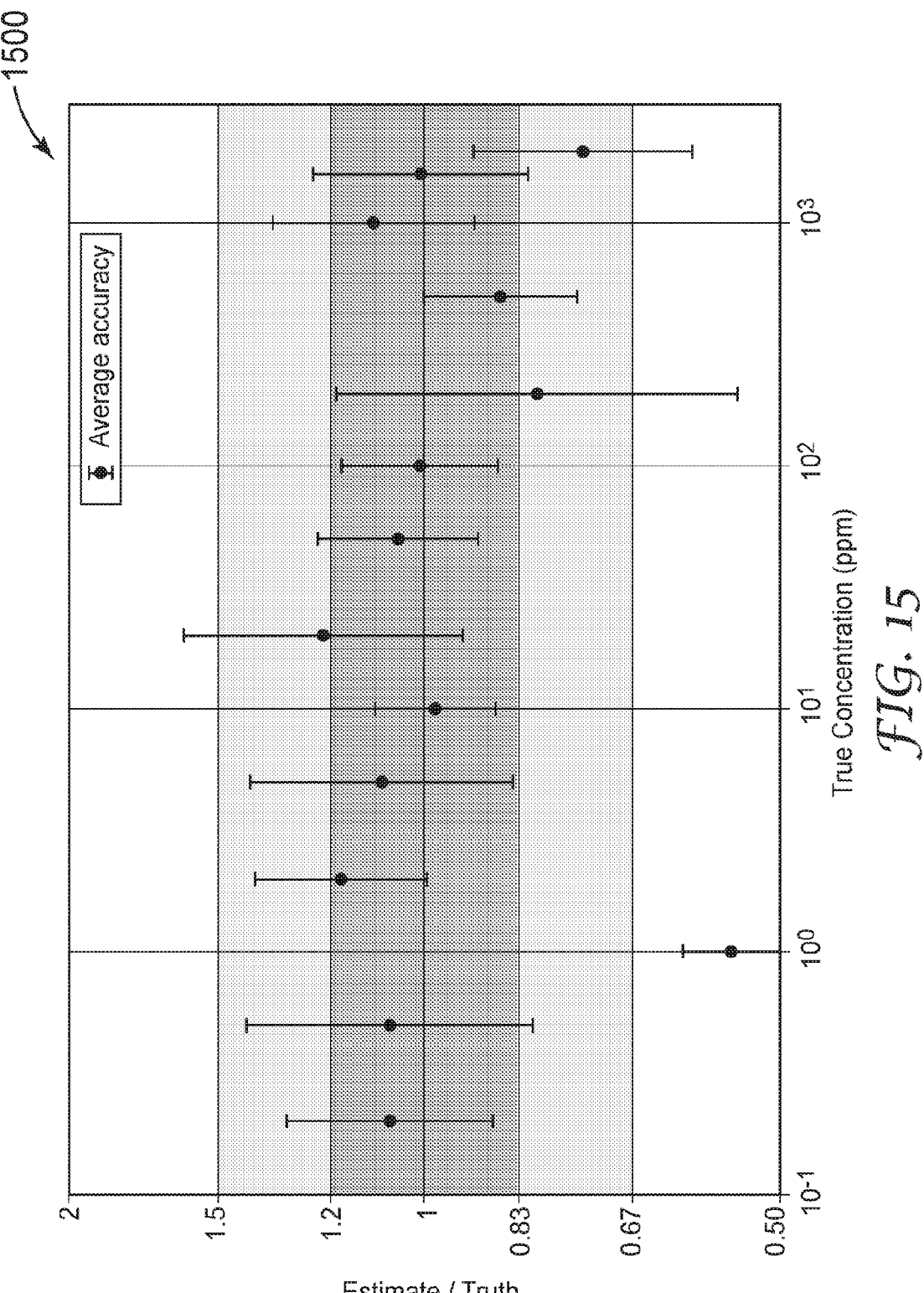
FIG. 15 illustrates a graph that shows the accuracy of analyte concentration outputs during a training phase of a model that reader devices and/or mobile computing devices may perform in accordance with the quantification techniques of this disclosure.

FIG. 15 illustrates graph 1500 that shows the accuracy of analyte concentration outputs during a training phase of a model that reader device 400 and/or smartphone 902 may perform in accordance with the quantification techniques of this disclosure. Each dot shows the actual accuracy, with the vertical lines (bounded by a respective floor and a respective ceiling) showing the accuracy of the estimates. The training device of this disclosure may also discern standard deviation and variance values form the accuracy of the training-phase estimates.

Again, while several mobile computing device-based techniques of this disclosure are described herein as being performed by smartphone 902, it will be appreciated that smartphone 902 is only one non-limiting example of mobile computing devices that may be configured to perform various techniques of this disclosure. Other examples of mobile computing devices that may be configured to perform various techniques attributed to smartphone 902 in this disclosure include, but are not limited to, tablet computers, wearable devices (e.g., smartwatches or smart glasses), personal digital assistants (PDAs), etc.

Figure 16:
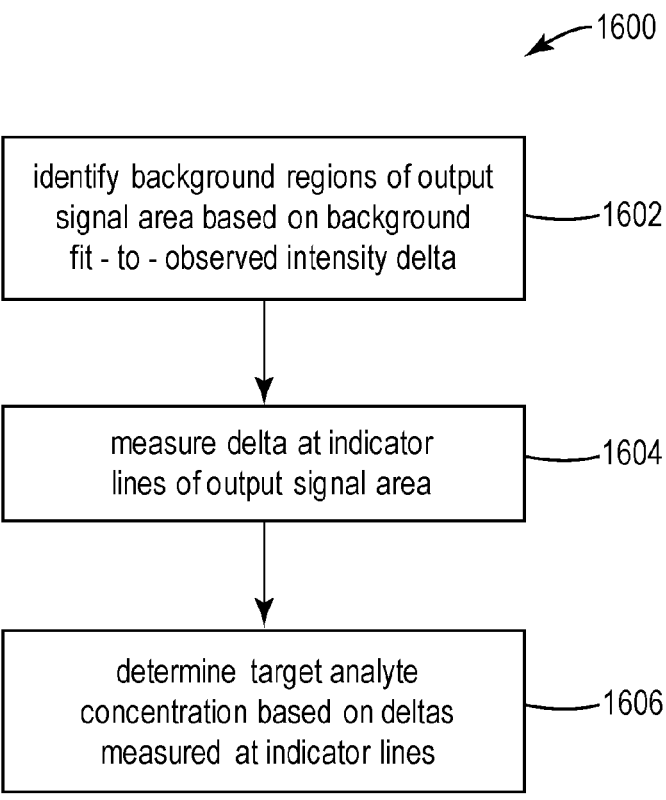
FIG. 16 is a flowchart illustrating an example process that reader devices and/or mobile computing devices of this disclosure may perform, in accordance with aspects of this disclosure.

FIG. 16 is a flowchart illustrating an example process 1600 that reader device 400 or smartphone 902 may perform, in accordance with aspects of this disclosure. As part of process 1600, reader device 400 or smartphone 902 identifies background regions of the output signal area of biological chromatographic test strip 410 based on background fit-to-observed intensity delta (1602). For instance, reader device 400 or smartphone 902 may identify the background regions using the techniques described above with respect to FIG. 13.

Reader device 400 or smartphone 902 may measure the deltas at the indicator lines of the output signal area of biological chromatographic test strip 410 (1604). For instance, reader device 400 or smartphone 902 may measure the "scores" illustrated in FIG. 13B. Based on the deltas measured at the indicator lines, reader device 400 or smartphone 902 may determine the target analyte concentration in the test sample submitted via biological test strip 410 (1606). In some examples, reader device 400 or smartphone 902 may determine a concentration range in which the target analyte concentration falls.

Figures 17A, 17B, 17C:
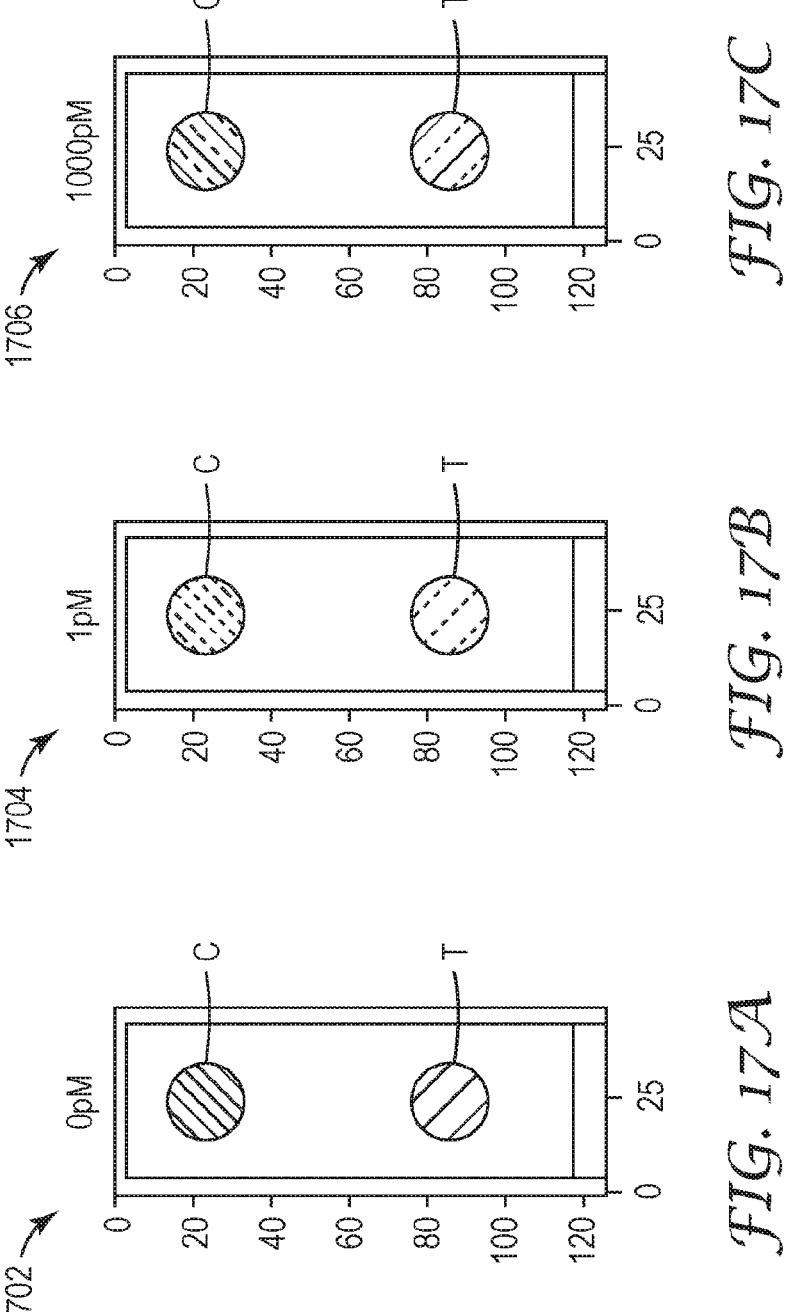
FIGS. 17A-17C illustrate illustrates additional examples of biological chromatographic test strips that reader devices and/or mobile computing devices of this disclosure may be configured to analyze for qualitative and/or quantitative results, according to aspects of this disclosure.

FIGS. 17A-17C illustrate biological chromatographic test strips 1702-1706 that reader device 400 or smartphone 902 may be configured to analyze for quantitative results, according to aspects of this disclosure. The output signal areas of biological chromatographic test strips 1702-1706 are of a different form factor than those of other biological chromatographic test strips, in that the respective output signal area of each of biological chromatographic test strips 1702-1706 includes two dots, namely, one control dot and one test dot. In the examples shown in FIGS. 17A-17C, biological chromatographic test strips 1702-1706 may be configured such that each of the control dot and the test dot changes color based on the concentration of the target analyte in the submitted test sample. Biological chromatographic test strips 1702-1706 are described herein as being used to test for the COVID-19 virus in human saliva test samples, with the concentration of the target analyte being expressed in picomolars (pM).

Biological chromatographic test strip 1702 is shown as outputting a readout for a negative result caused by a zero (0) pM concentration of the target analyte in the submitted test sample. Biological chromatographic test strip 1704 is shown as outputting a readout for a positive result caused by an approximately one (1) pM concentration of the target analyte in the submitted test sample. Biological chromatographic test strip 1706 is shown as outputting a readout for positive result caused by an approximately one thousand (1000) pM concentration of the target analyte in the submitted test sample. "C" denotes a control dot and "T"

denotes a test dot in each respective output signal area of biological chromatographic test strips 1702-1706.

The colorimetric facets of the respective control dots and test dots of biological chromatographic test strips 1702-1706 may change with target analyte concentrations in test samples, as shown by way of the three non-limiting examples illustrated in FIGS. 17A-17C. Reader device 400 or smartphone 902 may analyze the color intensity values of the control and test dots as well as ratios between the control and test dots of a single output area examined concurrently (or substantially concurrently) to determine the concentration of the target analyte in the submitted test sample.

Reader device 400 and smartphone 902 may be configured to implement "dot finder" logic to determine the locations of the control dot and the test dot in captured images representing the output signal areas of each of biological chromatographic test strips 1702-1706. The dot finder logic enables reader device 400 and smartphone 902 to search the captured image and identify solid circles (or solid shapes of substantially circular shape) that have a radius within a predefined range. In one non-limiting example, the dot finder logic may recognize a control or test dot based on detecting a circle having a radius between ten (10) and fifty-five (55) pixels. By using a specified range of acceptable radii, the dot finder logic enables reader device 400 and smartphone 902 to eliminate false positives that might be caused by imperfections, errant aberrations, or other noise in the appearance of the output signal area of any of biological chromatographic test strips 1702-1706. For example, the dot finder may search for pixel groupings that fall within the predefined radius range.

Using the captured image (e.g., a preprocessed version thereof, a grayscale version thereof, etc.), the dot finder logic locates substantially circular regions having a radius in the specified range in which the pixels vary in one or more color channel intensity from the rest of the image so as to constitute an indicator circle rather than noise. Upon identifying two such circular or substantially circular regions in the image using the dot finder logic, reader device 400 or smartphone 902 may evaluate colorimetric intensity values associated with the two dots (and ratios and/or other comparative indicators therebetween) to determine the concentration of the target analyte in the submitted test sample.

Reader device 400 and/or smartphone 902 may analyze images of biological chromatographic test strips 1702-1706 in various scenarios in which biological chromatographic test strips 1702-1706 follow different color schemes. For instance, reader device 400 and/or smartphone 902 may perform the techniques described herein whether the background of any of biological chromatographic test strips 1702-1706 may be white, gray, black, or any other color. In some examples, reader device 400 and/or smartphone 902 may perform the techniques described herein regardless of various color schemes to which the control dot and test dot conform (e.g., light blue and light green for negative results, darker blue and darker green for 1 pM results, even darker blue and even darker green for 1,000 pM results, etc.).

Although described herein with respect to analyzing output signal areas that display a control dots, it will be appreciated that, in other examples consistent with this disclosure, reader device 400 and/or smartphone 902 may analyze biological chromatographic test strips that output other types of output signals, such as regular polygons including rectangles, etc. In these examples, reader device 400 and/or smartphone 902 may implement polygon finder logic that identifies the output signal polygon using one or more dimensional descriptors of the pixel grouping, such as area, length, width, diagonal length (e.g., in the case of a rectangle), etc.

Also, while reader device 400 and smartphone 902 are described as analyzing control dots that change color and/or colorimetric intensity with target analyte presence/in the examples of biological chromatographic test strips 1702-1706, it will be appreciated that reader device 400 and/or smartphone 902 may be configured to analyze biological chromatographic test strips that output control dots that maintain a generally consistent color in a variety of scenarios, and sometimes, generally match the color and/or colorimetric intensity of the test dot in a particular test result scenario (e.g., negative, or at a particular target analyte concentration range for positive test results).

Additionally, while reader device 400 and smartphone 902 are described as analyzing change color and/or colorimetric intensity data with respect to biological chromatographic test strips 1702-1706, it will be appreciated that reader device 400 and/or smartphone 902 may be configured to analyze fluorescence-based signals from biological chromatographic test strips, as well, with respect to dots or differently shaped output signals. Additionally, while reader device 400 and smartphone 902 are described as analyzing biological chromatographic test strips 1702-1706 for quantitative results, it will be appreciated that reader device 400 and/or smartphone 902 may, in some examples, analyze biological chromatographic test strips 1702-1706 for qualitative results (e.g., a binary positive vs. negative decision regarding target analyte presence in the test sample, etc.). Reader device 400 and/or smartphone 902 may implement, with respect to biological chromatographic test strips that output indicator signals of rounded shapes or polygon-based shapes, techniques generally corresponding to any one or more of the techniques described above with respect to FIGS. 1-16.

Figure 18A:
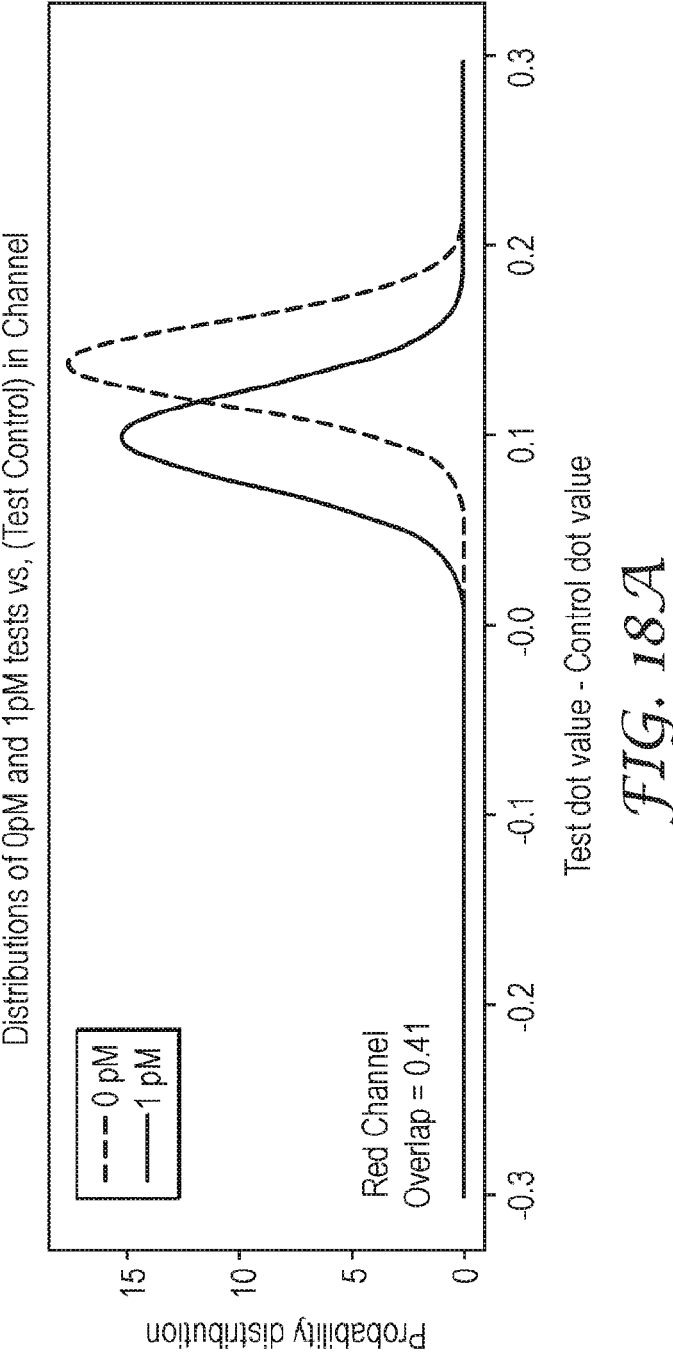
FIGS. 18A-18F are graphs illustrating colorimetric intensity transitions of the control dot and test dot of various biological chromatographic test strips that produce negative results and that produce positive results based on a one (1) picomolar target analyte concentration.
Figure 18B:
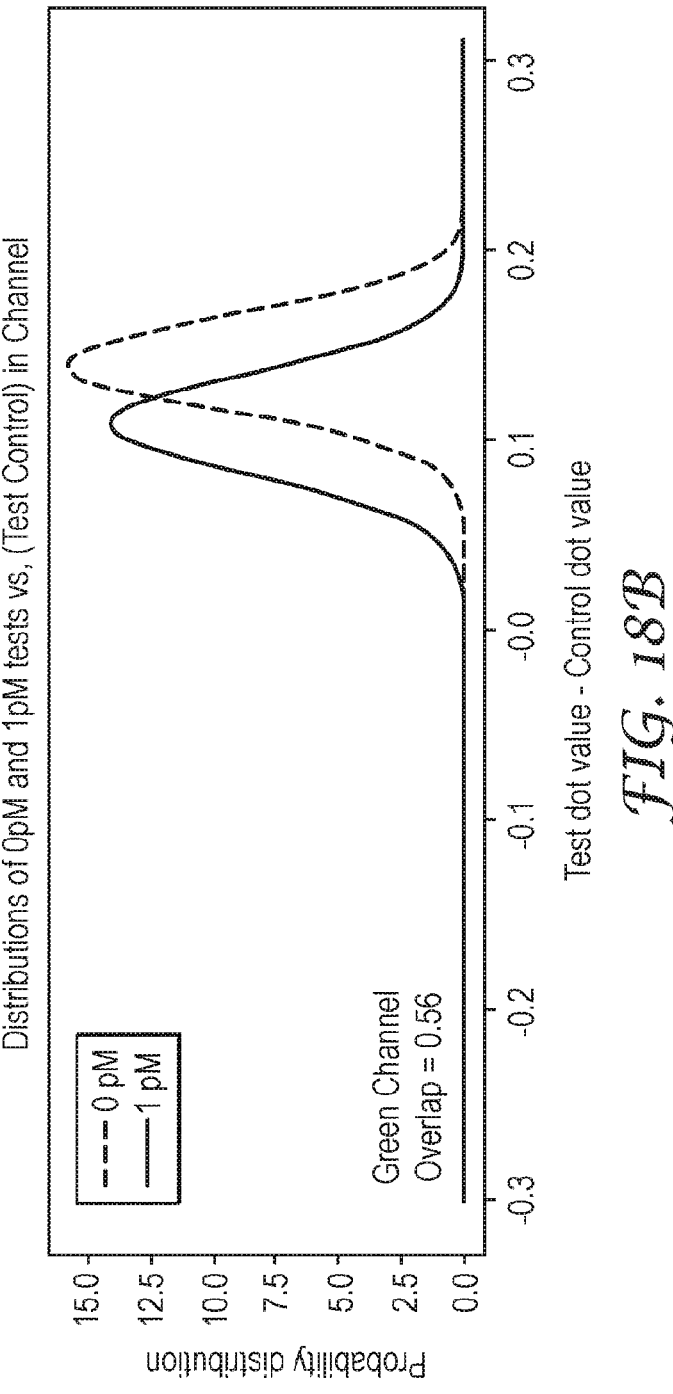
Figure 18C:
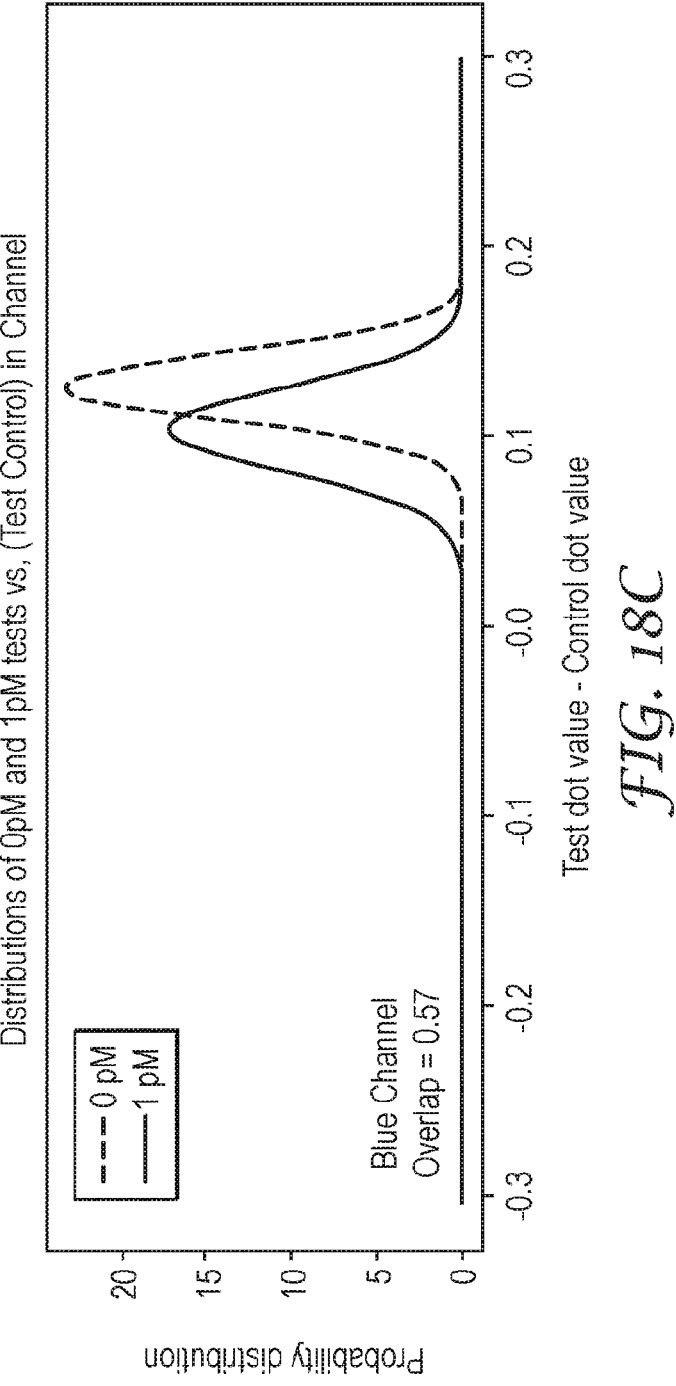
Figure 18D:
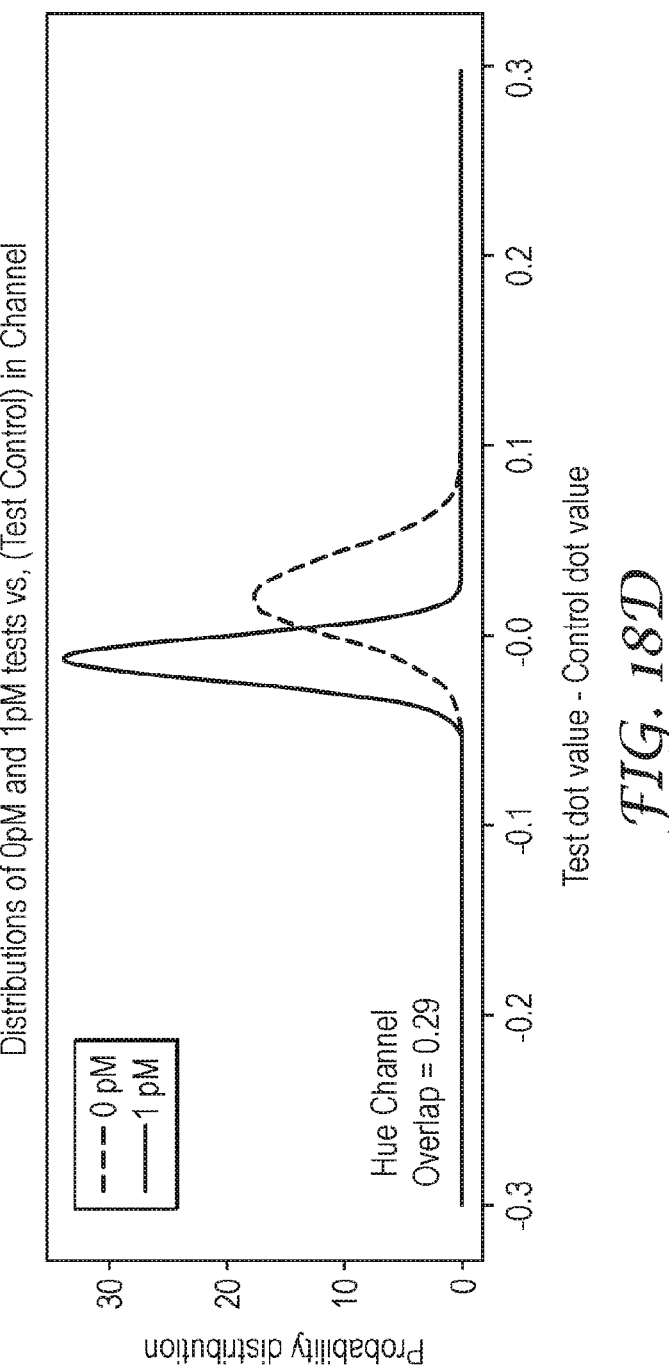
Figure 18E:
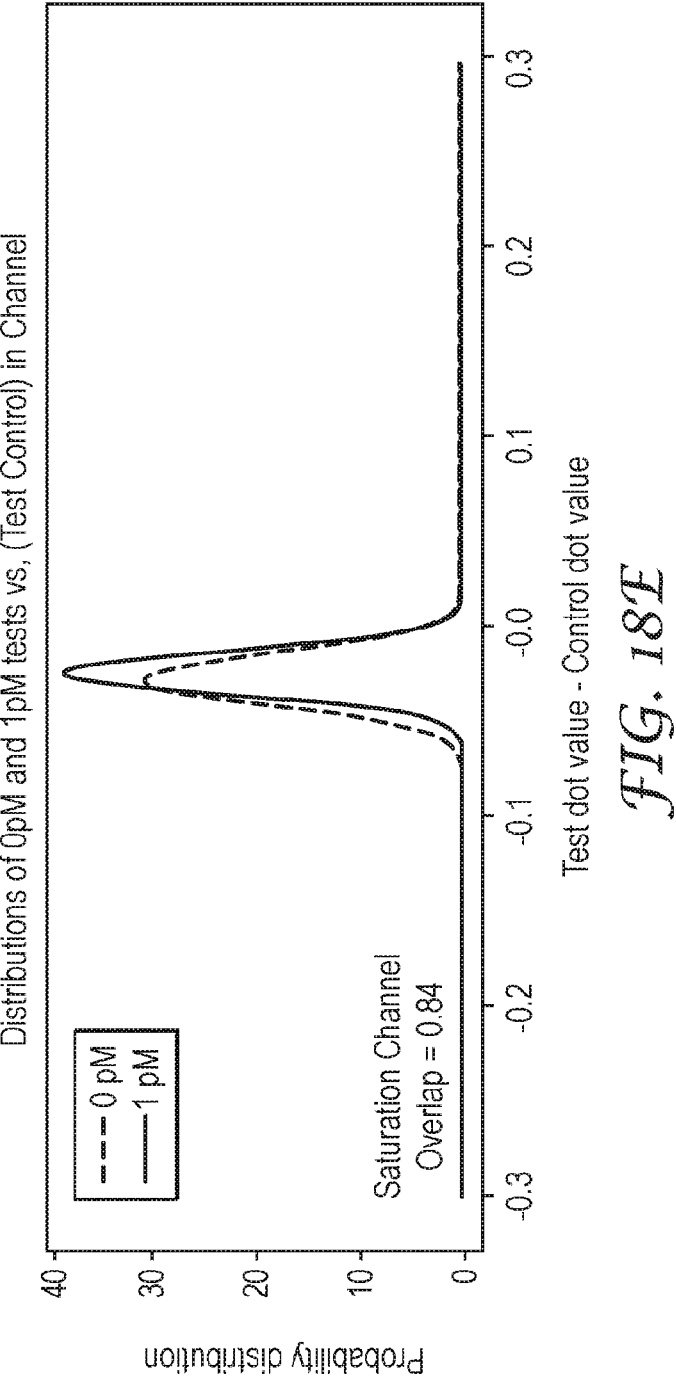
Figure 18F:
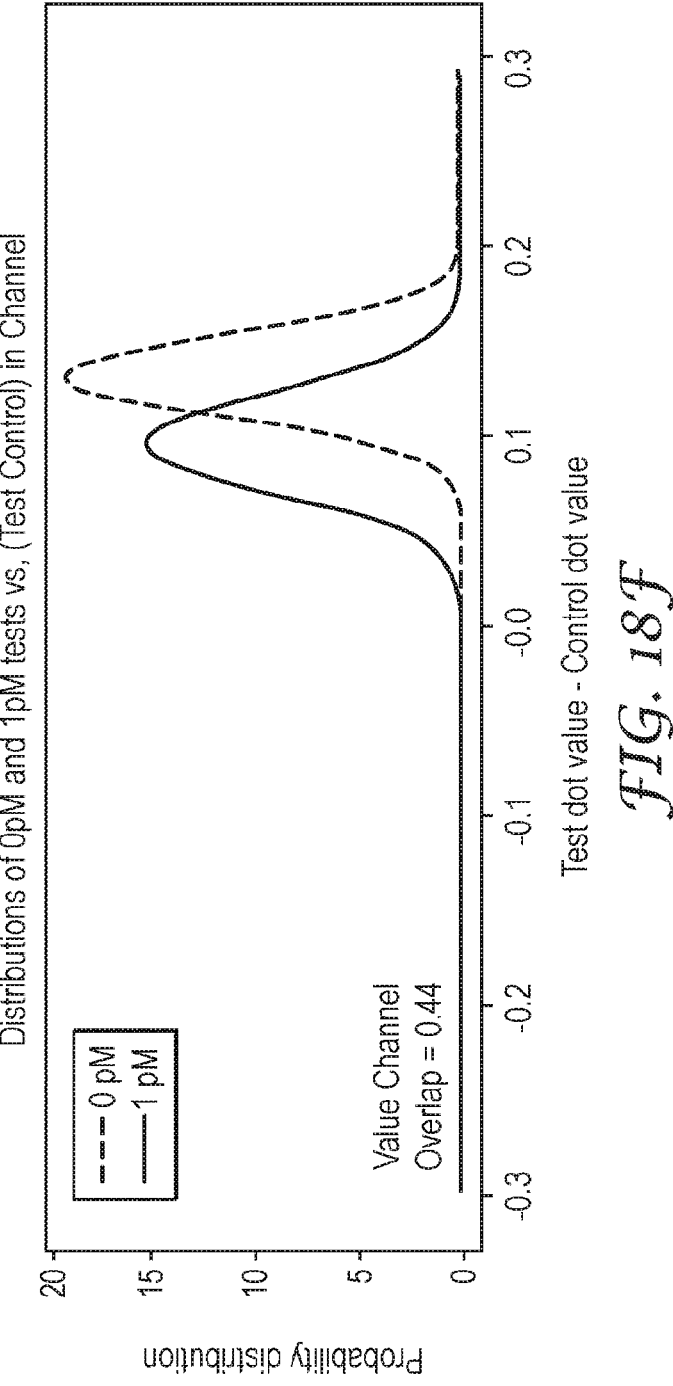

FIGS. 18A-18F are graphs illustrating colorimetric intensity transitions of the control dot and test dot of various biological chromatographic test strips that produce negative results and that produce positive results based on a one (1) pM target analyte concentration. Biological chromatographic test strips 1702 and 1704 may be included in the data points that produce the colorimetric intensity transitions shown in FIGS. 18A-18F. FIGS. 18A, 18B, and 18C illustrate colorimetric intensity transitions in the red, green, and blue color channels, respectively, of the RGB color space. FIGS. 18D, 18E, and 18F illustrate colorimetric intensity transitions in the hue, saturation, and value color channels, respectively. As used herein: (i) "hue" refers to similarity to one of red, orange, yellow, green, blue, or purple on a color spectrum; (ii) "saturation" refers to similarity to pure color (or alternatively, difference from gray); and (iii) "value" refers to brightness or luminance ranging from black to white.

In the particular example of FIGS. 18A-18F, which illustrate a quantitative result of 1 pM for the positive test as opposed to a negative (0 pM) test, the hue channel yields the most reliable detection scheme. The overlap value of 0.29 shown in FIG. 18D indicates a test accuracy of 71% in the hue channel. In this scenario, reader device 400 or smartphone 902 may assign a greater weight to the hue channel than to the remaining channels in performing image-based quantitative analysis. In some examples, reader device 400 or smartphone 902 may assign a lesser weight or may disregard less reliable color channels for a particular analysis, such as the saturation channel in the particular case of FIGS. 18A-18F.

Figure 19A:
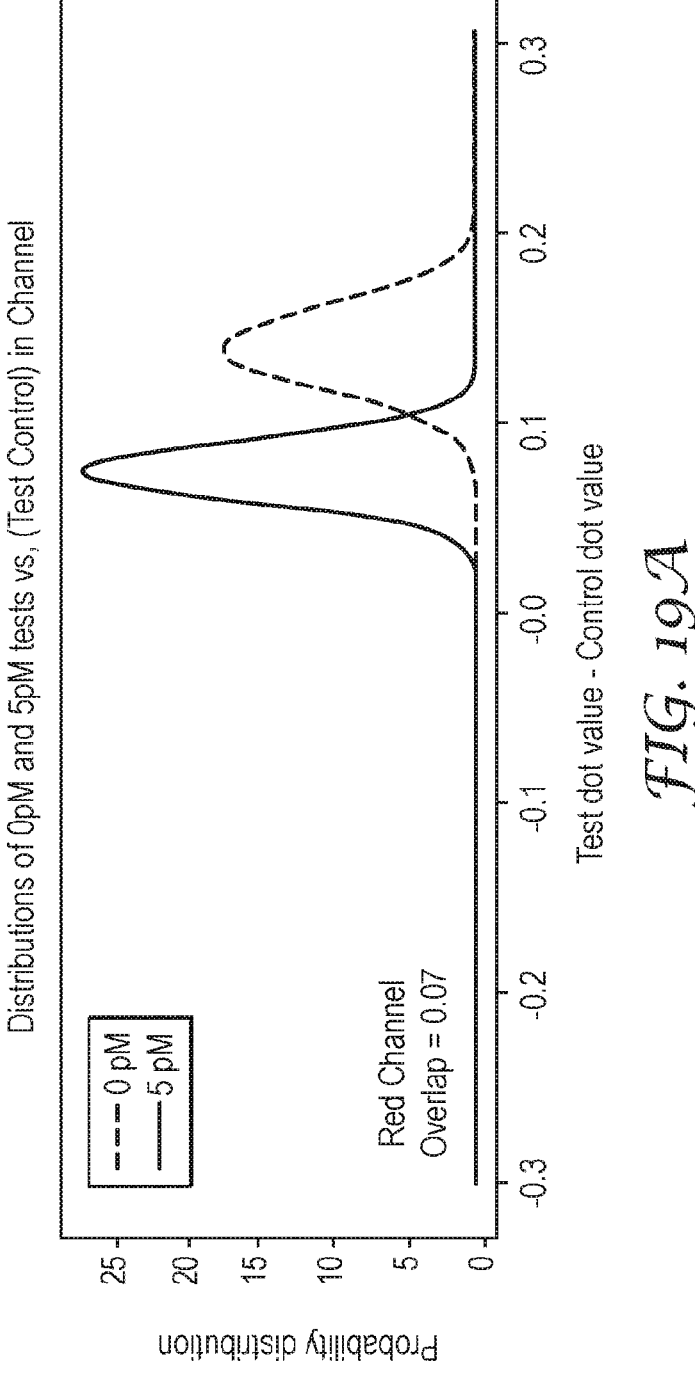
FIGS. 19A-19F are graphs illustrating colorimetric intensity transitions of the control dot and test dot of various biological chromatographic test strips that produce negative results and that produce positive results based on a five (5) picomolar target analyte concentration.
Figure 19B:
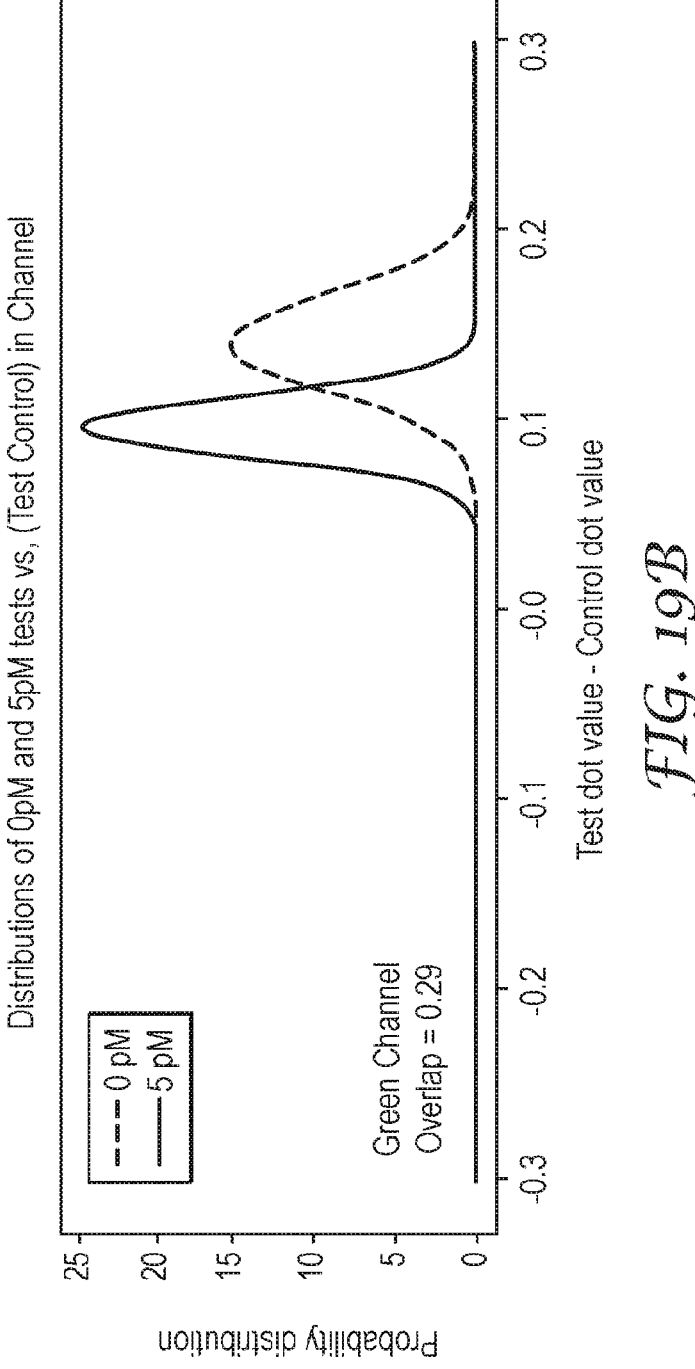
Figure 19C:
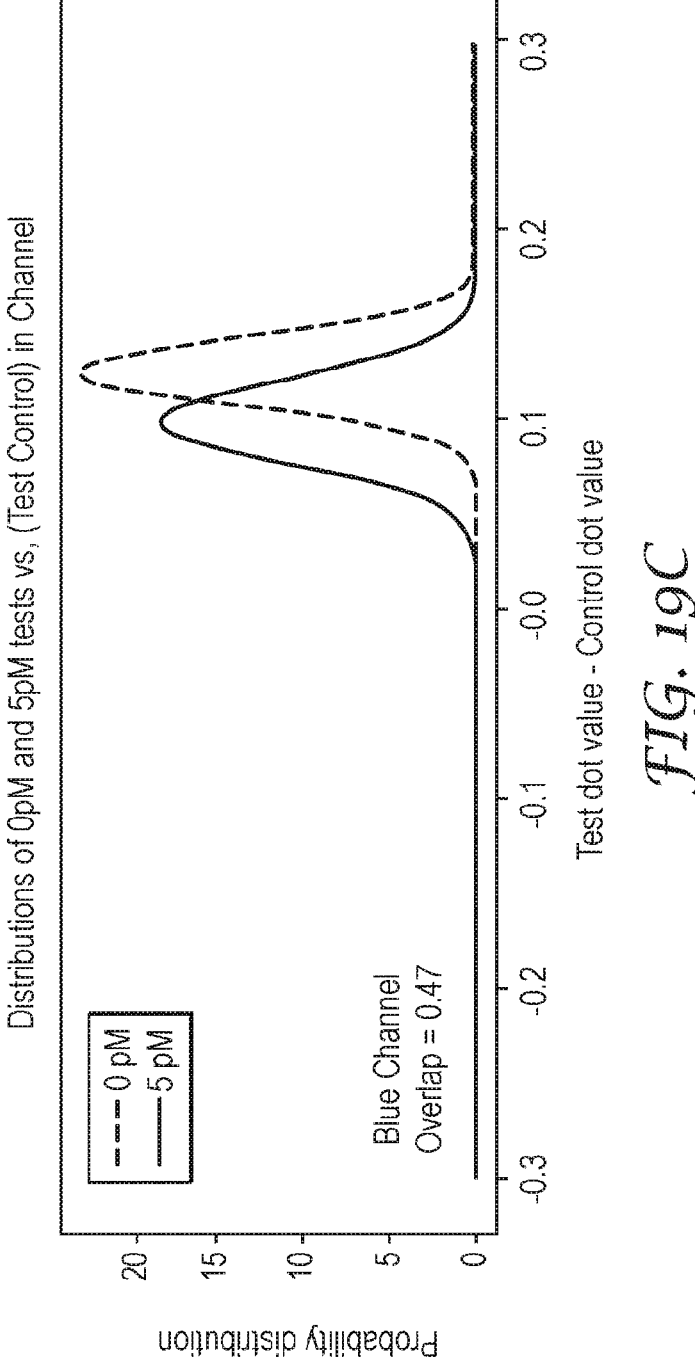
Figure 19D:
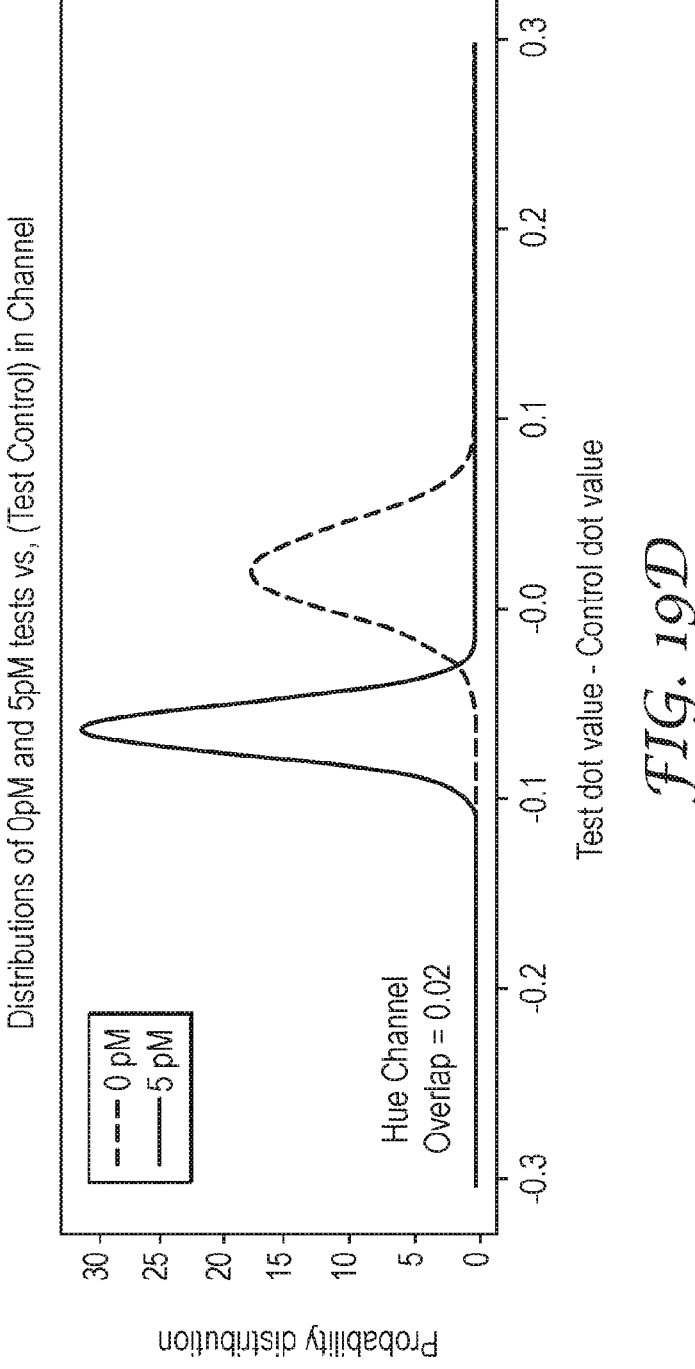
Figure 19E:
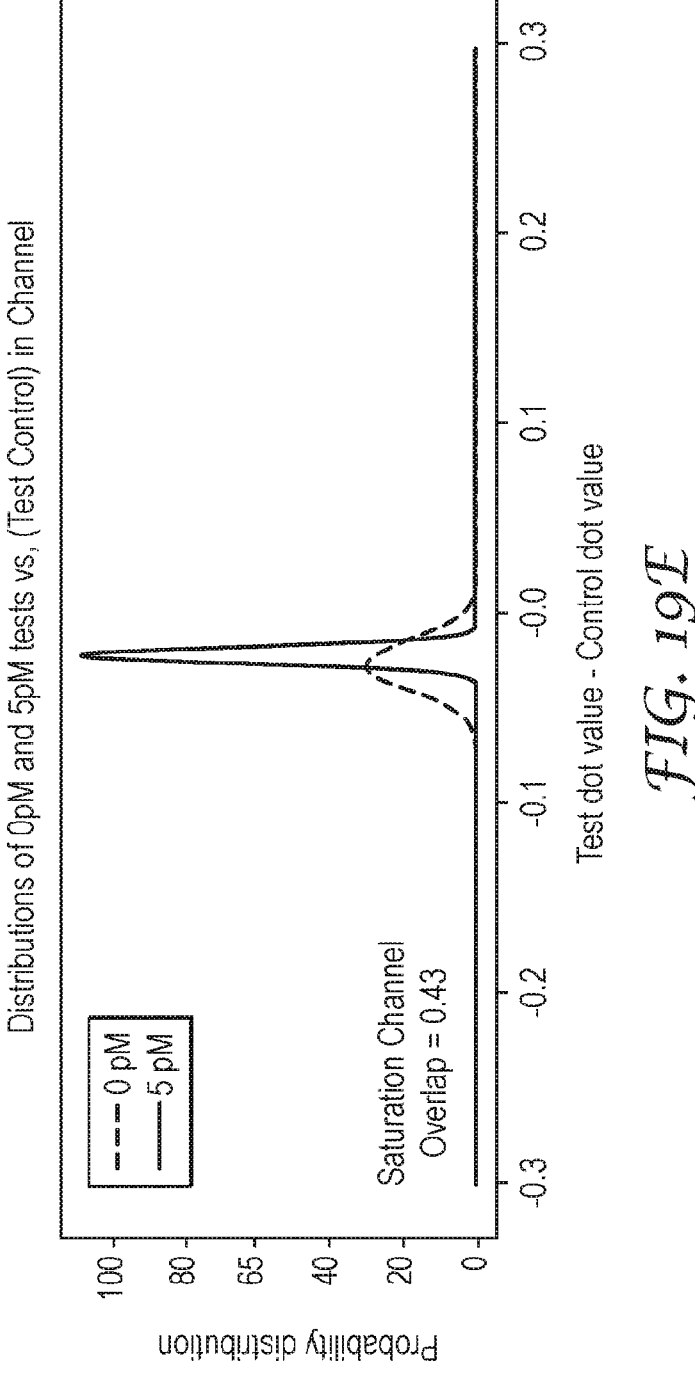
Figure 19F:
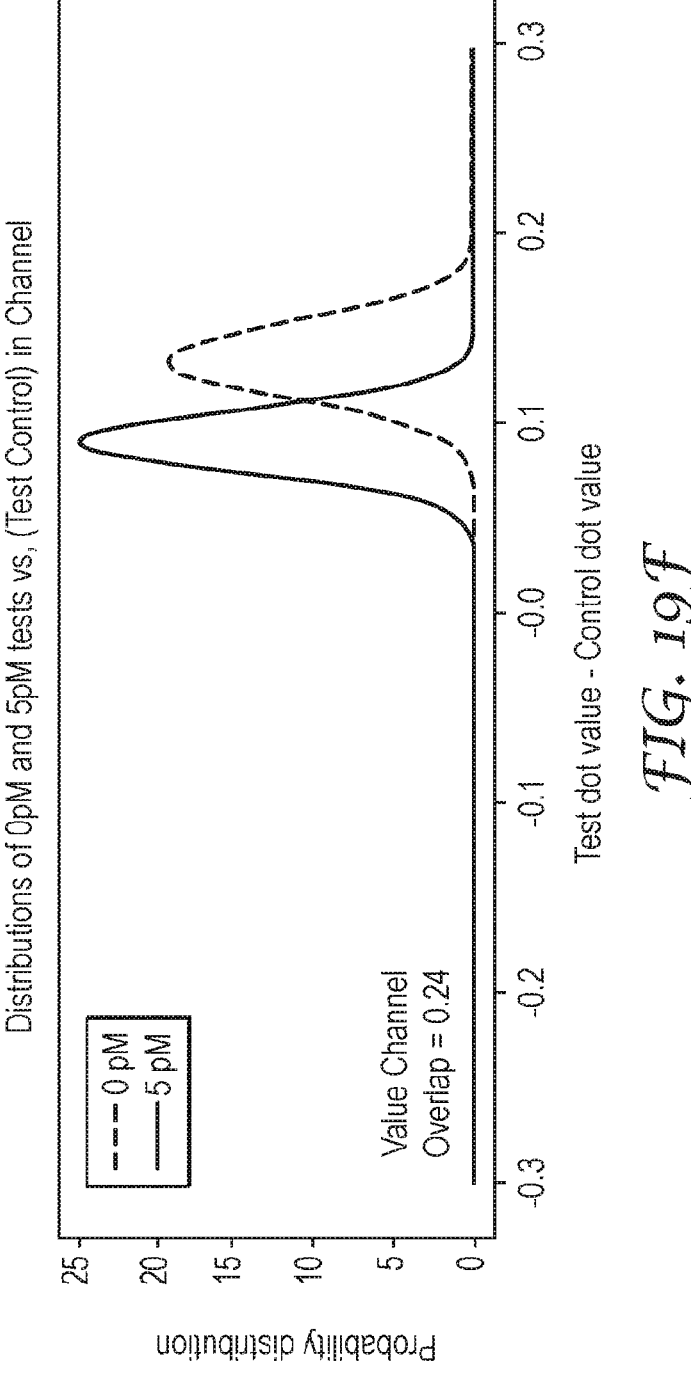

FIGS. 19A-19F are graphs illustrating colorimetric intensity transitions of the control dot and test dot of various biological chromatographic test strips that produce negative results and that produce positive results based on a five (5) pM target analyte concentration. FIGS. 19A, 19B, and 19C illustrate colorimetric intensity transitions in the red, green, and blue color channels, respectively, of the RGB color space. FIGS. 19D, 19E, and 19F illustrate colorimetric intensity transitions in the hue, saturation, and value color channels, respectively. In the particular example of FIGS. 19A-19F, which illustrate a quantitative result of 5 pM for the positive test as opposed to a negative (0 pM) test, the hue channel yields the most reliable detection scheme. The overlap value of 0.02 shown in FIG. 19D indicates a test accuracy of 98% in the hue channel.

In the particular example of FIGS. 19A-19F, the red channel yields the second most reliable detection scheme. The overlap value of 0.07 shown in FIG. 19D indicates a test accuracy of 93% in the hue channel. In this scenario, reader device 400 or smartphone 902 may assign greater weights to the hue channel and the red channel than to the remaining channels in performing image-based quantitative analysis. For example, FIGS. 19A-19F may represent colorimetric intensity transition end states for control and test dots that, in one case, absorb red light well, while in the other case, reflect red light well. In some examples, reader device 400 or smartphone 902 may assign a lesser weight or may disregard less reliable color channels for a particular analysis, such as the blue channel and/or the saturation channel in the particular case of FIGS. 19A-19F.

Figure 20:
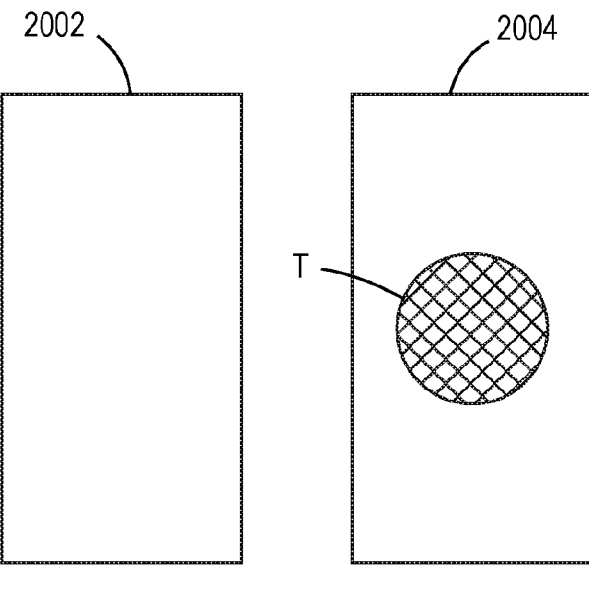
FIG. 20 illustrates additional examples of biological chromatographic test strips that reader devices of this disclosure may be configured to analyze for quantitative results, according to aspects of this disclosure.

FIG. 20 illustrates biological chromatographic test strips 2002 and 2004 that reader device 400 or smartphone 902 may be configured to analyze for quantitative results, according to aspects of this disclosure. The output signal areas of biological chromatographic test strips 2002 and 2004 differ from the output signal areas of biological chromatographic test strips 1702-1706 in a number of ways. As one example, the negative test result (or pre-sample-submission state) of biological chromatographic test strip 2002 does not show any readily visible output signals. As another example, the positive test result of biological chromatographic test strip 2004 includes only one visible output signal, namely, a test dot. In some examples, reader device 400 or smartphone 902 may implement the dot finder logic described above to identify the test dot in biological chromatographic test strip 2004. In other examples, reader device 400 or smartphone 902 may implement the background fit-based techniques described above to identify the test dot in biological chromatographic test strip 2004. In various examples, reader device 400 or smartphone 902 may detect the test dot of biological chromatographic test strip 2004 at varying levels of colorimetric transition granularity (e.g. by distinguishing off-white from white, in a relatively sensitive example).

In various examples, reader device 400 and/or smartphone 902 may represent "universal readers" in that reader device 400 and/or smartphone 902 can be configured to analyze images of output areas of different form factors (e.g., as shown by way of biological chromatographic test strips 1702-1706, biological chromatographic test strips 2002 & 2004, or biological chromatographic test strips 302-314). In some examples, reader device 400 and/or smartphone 902 may provide an interactive user interface (UI) that accepts user input specifying the form factor the output signal area(s) to be read. In some examples, reader device 400 and/or smartphone 902 may provide an interactive UI that accepts user input specifying further details of the output signal area(s) to be read, such as the number of lines to be searched, the number of dots to be searched, the lower threshold for a dot radius, the upper threshold for a dot radius, etc. In some examples, reader device 400 and/or smartphone 902 may provide an interactive UI that accepts user input that elicits outputs specifying test parameters, such as the limit of detection (e.g., the lowest concentration at which the target analyte can be detected, the highest concentration at which the target analyte can be detected, a choice between a binary positive/negative result and a quantitative result, etc.).

<center>Example</center>

FIG. 2 illustrates different test results detected by various biological chromatographic test strips of similar construction. Biological chromatographic test strips 302-314 each represents an individual test result as described below. As in the example of FIG. 1, the respective output signal areas of each of test strips 302-312 include areas for three indicator lines, namely, a control ('C') line, a hook ('H') line, and a test ('T') line.

Biological chromatographic test strip 302 indicates a defective test. Biological chromatographic test strip 304 indicates a negative test result, and each of biological chromatographic test strips 306-312 indicates a positive test result. Biological chromatographic test strip 314 indicates an invalid (e.g., inconclusive) test result. The invalid test result in the case of biological chromatographic test strip 314 may be due to various issues with the submitted test sample, including, but not limited to, the various types of defects described above with respect to biological chromatographic test strip 208 of FIG. 1, such as a target analyte concentration exceeding an upper threshold for generating valid test results. The negative test result in the case biological chromatographic test strip 304 may be due to reasons including, but not limited to, reasons described above with respect to biological chromatographic test strip 206 (e.g., sub-lower threshold concentration of the target analyte) of FIG. 1. The defective state in the case of biological chromatographic test strip 302 may be due to one or more of various factors, such as structural damage to biological chromatographic test strip 302, flow issue caused by solids in the test sample or any other obstructions of capillary action within the working of biological chromatographic test strip 302, chemical or bio-chemical changes in the conjugate material or the bound chemicals, etc.

In the instances of biological chromatographic test strips 306-312, the reader uses the individual color intensities of the respective test lines and the relative color intensities of the respective test lines with one or both of the control and/or hook lines of the same strip to determine a range in which the concentration of the target analyte in the test sample that triggered the positive test result falls. In the case of biological chromatographic test strip 306, the reader analyzes the individual and relative color intensities of the test line to determine that the target analyte is present in the test sample in a range of two (2) to ten (10) ppm.

In the case of biological chromatographic test strip 308, the reader analyzes the individual and relative color intensities of the test line to determine that the target analyte is present in the test sample in a range of ten (10) to fifty (50) ppm. In the case of biological chromatographic test strip 310, the reader analyzes the individual and relative color intensities of the test line to determine that the target analyte is present in the test sample in a range of fifty (50) to one thousand (1,000) ppm. In the case of biological chromatographic test strip 312, the reader analyzes the individual and relative color intensities of the test line to determine that the target analyte is present in the test sample in a range of over one thousand (1,000) ppm, but within an upper limit or upper threshold concentration.

The reader uses optical signals, such as colorimetric and/or fluorescent signals to generate the results described above with respect to biological chromatographic test strips 306-312, by implementing a quantitative signal-to-analyte algorithm using one or more red-green-blue (RGB) triplets to discern the quantity (or a range thereof) of the target analyte in the test sample submitted via the biodetection test strip.

In this example, the reader uses one or more control or reference area(s) in the output signal area of the biological chromatographic test strips to scale the signal (e.g., lines detected via colorimetric or fluorescence detection-based techniques) detected in the output signal area. The reader implements logic that uses a combination of target analyte indicator signals and signals from other control or reference area(s) to define a test result that is invalid. In this example, the logic implemented by the reader devices also executes a trained model (e.g., an artificial neural network) to draw an inference from signal(s) detected from the output signal areas of biological chromatographic test strips 306-312.

Example 1A: An apparatus comprising a mobile computing device physically coupled to a lightbox, the mobile computing device comprising: camera hardware configured to capture image data associated with an output signal area of a biological chromatographic test strip inserted into a receiving slot of the lightbox; processing circuitry in communication with the camera hardware, the processing circuitry being configured to: determine, based on the image data captured by the camera hardware, (i) an intensity of a control line displayed in the output signal area of the biological chromatographic test strip, (ii) an intensity of a hook line displayed in the output signal area of the biological chromatographic test strip, and (iii) an intensity of a test line displayed in the output signal area of the biological chromatographic test strip; determine a relative intensity between the test line and at least one of the hook line or control line using the intensity of the test line and at least one of the intensity of the hook line or the intensity of the control line; and detect, based on the relative intensity, a presence of a target analyte in a test sample submitted via the biological chromatographic test strip.

Example 2A: The apparatus of Example 1A, the processing circuitry being further configured to determine, based on the relative intensity, a concentration of the target analyte in the test sample submitted via the biological chromatographic test strip.

Example 3A: The apparatus of any of Examples 1A-2A, wherein the respective intensities of the control line, the hook line, and the test line represent colorimetric intensities.

Example 4A: The apparatus of Example 3A, wherein the colorimetric intensities represent intensities along individual color channels of an RGB color space.

Example 5A: The apparatus of any of Examples 1A-4A, wherein the mobile computing device is a smartphone.

Example 6A: The apparatus of Example 5A, wherein the camera hardware is included in a rear-facing camera of the smartphone.

Example 7A: The apparatus of Example 5A, wherein the camera hardware is included in a front-facing camera of the smartphone.

Example 8A: The apparatus of any of Examples 1A-4A, wherein the mobile computing device is a tablet computer.

Example 9A: The apparatus of any of Examples 1A-8A, wherein the interface is a touchscreen display.

Example 10A: The apparatus of any of Examples 1A-9A, wherein an inner surface of the lightbox comprises a reflective surface configured to reflect light emitted by a light source positioned near lens hardware of the camera hardware.

Example 11A: The apparatus of any of Examples 1A-9A, wherein an inner surface of the lightbox comprises a light cavity configured to provide backlighting of the biological chromatographic test strip.

Example 1B: An apparatus comprising a mobile computing device physically coupled to a lightbox comprising: camera hardware configured to capture image data associated with an output signal area of a biological chromatographic test strip inserted into a receiving slot of the lightbox; processing circuitry in communication with the camera hardware, the processing circuitry being configured to determine, based on the image data captured by the camera hardware, a concentration of a target analyte in a test sample submitted via the biological chromatographic test strip; and an interface in communication with the processing circuitry, the interface being configured to output data indicative of the concentration of the target analyte determined by the processing circuitry.

Example 2B: The apparatus of Example 1B, wherein to determine the concentration of the target analyte in the test sample, the processing circuitry is configured to: determine, based on the image data captured by the camera hardware, (i) an intensity of a control line displayed in the output signal area of the biological chromatographic test strip, (ii) an intensity of a hook line displayed in the output signal area of the biological chromatographic test strip, and (iii) an intensity of a test line displayed in the output signal area of the biological chromatographic test strip; determine a relative intensity between the test line and at least one of the hook line or control line using the intensity of the test line and at least one of the intensity of the hook line or the intensity of the control line; and determine the concentration of the target analyte based on the relative intensity.

Example 3B: The apparatus of any of Examples 1B-2B, wherein the mobile computing device is a smartphone.

Example 4B: The apparatus of Example 3B, wherein the camera hardware is included in a rear-facing camera of the smartphone.

Example 5B: The apparatus of Example 3B, wherein the camera hardware is included in a front-facing camera of the smartphone.

Example 6B: The apparatus of any of Examples 1B-2B, wherein the mobile computing device is a tablet computer.

Example 7B: The apparatus of any of Examples 1B-7B, wherein the interface is a touchscreen display.

Example 8B: The apparatus of any of Examples 1B-7B, wherein an inner surface of the lightbox comprises a reflective surface configured to reflect light emitted by a light source positioned near lens hardware of the camera hardware.

Example 9B: The apparatus of any of Examples 1B-7B, wherein an inner surface of the lightbox comprises a light cavity configured to provide backlighting of the biological chromatographic test strip.

Devices and systems of this disclosure may include, in addition to processors or processing circuitry (e.g., fixed function circuitry and/or programmable circuitry), various types of memory. Memory devices or components of this disclosure may include a computer-readable storage medium or computer-readable storage device. In some examples, the memory includes one or more of a short-term memory or a long-term memory. The memory may include, for example, RAM, DRAM, SRAM, magnetic discs, optical discs, flash memories, or forms of EPROM, or EEPROM. In some examples, the memory is used to store program instructions for execution by processors or processing circuitry (e.g., fixed function circuitry and/or programmable circuitry), communicatively coupled thereto. The memory may be used by software or applications running on various devices or systems to temporarily store information during program execution.

If implemented in software, the techniques may be realized at least in part by a computer-readable medium comprising instructions that, when executed in a processor, performs one or more of the methods described above. The computer-readable medium may comprise a tangible computer-readable storage medium and may form part of a computer program product, which may include packaging materials. The computer-readable storage medium may comprise random access memory (RAM) such as synchronous dynamic random access memory (SDRAM), read-only memory (ROM), non-volatile random access memory (NVRAM), electrically erasable programmable read-only memory (EEPROM), FLASH memory, magnetic or optical data storage media, and the like. The computer-readable storage medium may also comprise a non-volatile storage device, such as a hard-disk, magnetic tape, a compact disk (CD), digital versatile disk (DVD), Blu-ray disk, holographic data storage media, or other non-volatile storage device.

The term "processor," as used herein may refer to any of the foregoing structure or any other structure suitable for implementation of the techniques described herein. In addition, in some aspects, the functionality described herein may be provided within dedicated software modules or hardware modules configured for performing the techniques of this disclosure. Even if implemented in software, the techniques may use hardware such as a processor to execute the software, and a memory to store the software. In any such cases, the computers described herein may define a specific machine that is capable of executing the specific functions described herein. Also, the techniques could be fully implemented in one or more circuits or logic elements, which could also be considered a processor or processing circuitry (e.g., fixed function circuitry and/or programmable circuitry).

In one or more examples, the functions described may be implemented in hardware, software, firmware, or any combination thereof. If implemented in software, the functions may be stored on or transmitted over, as one or more instructions or code, a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media, which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transient media, but are instead directed to non-transient, tangible storage media. Disk and disc, as used, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Instructions may be executed by one or more processors, such as one or more digital signal processors (DSPs), general purpose microprocessors, processing circuitry (e.g., fixed function circuitry and/or programmable circuitry), application specific integrated circuits (ASICs), field programmable logic arrays (FPGAs), or other equivalent integrated or discrete logic circuitry. Accordingly, the term "processor", as used may refer to any of the foregoing structure or any other structure suitable for implementation of the techniques described. In addition, in some aspects, the functionality described may be provided within dedicated hardware and/or software modules. Also, the techniques could be fully implemented in one or more circuits or logic elements.

The techniques of this disclosure may be implemented in a wide variety of devices or apparatuses, including a wireless handset, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperative hardware units, including one or more processors as described above, in conjunction with suitable software and/or firmware.

It is to be recognized that depending on the example, certain acts or events of any of the methods described herein can be performed in a different sequence, may be added, merged, or left out altogether (e.g., not all described acts or events are necessary for the practice of the method). Moreover, in certain examples, acts or events may be performed concurrently, e.g., through multi-threaded processing, interrupt processing, or multiple processors, etc. In some examples, a computer-readable storage medium includes a non-transitory medium. The term "non-transitory" indicates, in some examples, that the storage medium is not embodied in a carrier wave or a propagated signal. In certain examples, a non-transitory storage medium stores data that can, over time, change (e.g., in RAM or cache). rather than sequentially.

Although specific embodiments have been illustrated and described herein, any arrangement that achieve the same purpose, structure, or function may be substituted for the specific embodiments shown. This application is intended to cover any adaptations or variations of the example embodiments of the invention described herein. These and other embodiments are within the scope of the following claims and their equivalents.

What is claimed is:

1. An apparatus comprising a mobile computing device physically coupled to a lightbox, the mobile computing device comprising:

camera hardware configured to capture image data associated with an output signal area of a biological chromatographic test strip inserted into a receiving slot of the lightbox;

processing circuitry in communication with the camera hardware, the processing circuitry being configured to:

determine, using an intensity of a background fit section represented in the image data captured by the camera hardware, (i) an intensity of a control line displayed in the output signal area of the biological chromatographic test strip at least in part by determining an offset between a true channel brightness of the control line and a true channel brightness of the background fit section as represented by a depth of a trough associated with the true channel brightness of the control line, (ii) an intensity of a hook line displayed in the output signal area of the biological chromatographic test strip based on an intensity offset between one or more attributes of the hook line and the intensity of the background fit section at least in part by determining an offset between a true channel brightness of the hook line and the true channel brightness of the background fit section as represented by a depth of a trough associated with the true channel brightness of the hook line, and (iii) an intensity of a test line displayed in the output signal area of the biological chromatographic test strip at least in part by determining an offset between a true channel brightness of the test line and a true channel brightness of the background fit section as represented by a depth of a trough associated with the true channel brightness of the test line, wherein respective offsets determined for the control line, the hook line, and the test line are determined for each color channel of a red-green-blue (RGB) color space and summed to obtain a full-color delta for each respective line;

determine, based on the intensity of the hook line, that a test sample submitted via the biological chromatographic test strip is of a sufficient concentration to perform analysis with respect to a target analyte in the test sample;

based on the determination that the test sample submitted via the biological chromatographic test strip is of the sufficient concentration to perform the analysis with respect to the target analyte in the test sample, determine a relative intensity between the test line and at least one of the hook line or control line using the intensity of the test line and at least one of the intensity of the hook line or the intensity of the control line; and determine, based on the relative intensity, a quantity of the target analyte present in the test sample submitted via the biological chromatographic test strip.

2. The apparatus of claim 1, wherein to determine the quantity of the target analyte present in the test sample submitted via the biological chromatographic test strip, the processing circuitry is configured to determine, based on the relative intensity, a concentration of the target analyte in the test sample submitted via the biological chromatographic test strip.

3. The apparatus of claim 1, wherein the mobile computing device is a smartphone.

4. The apparatus of claim 3, wherein the camera hardware is included in one of a rear-facing camera of the smartphone or in a front-facing camera of the smartphone.

5. The apparatus of claim 1, wherein the mobile computing device is a tablet computer.

6. The apparatus of claim 1, wherein an inner surface of the lightbox comprises a reflective surface configured to reflect light emitted by a light source positioned near lens hardware of the camera hardware.

7. The apparatus of claim 1, wherein an inner surface of the lightbox comprises a light cavity configured to provide backlighting of the biological chromatographic test strip.

8. The apparatus of claim 2, wherein the processing circuitry is further configured to execute an algorithm to compare the determined concentration against a reference template or reference function.

9. The apparatus of claim 8, wherein the algorithm is an artificial neural network.

10. The apparatus of claim 1, wherein the processing circuitry is further configured to decompose portions of the image data representing the test line, the hook line, and the control line into red, green, and blue color channels.

11. The apparatus of claim 10, wherein the processing circuitry is further configured to determine respective differences between the background fit section and each of the test line the hook line, and the control line in each of the red, green, and blue color channels.

12. The apparatus of claim 1, wherein to determine the relative intensity, the processing circuitry is further configured to execute a trained model to draw one or more inferences from one or more signals detected from the output signal area.

13. An apparatus comprising a mobile computing device physically coupled to a lightbox comprising:

camera hardware configured to capture image data associated with an output signal area of a biological chromatographic test strip inserted into a receiving slot of the lightbox;

processing circuitry in communication with the camera hardware, the processing circuitry being configured to:

determine, using an intensity of a background fit section represented in the image data captured by the camera hardware, (i) an intensity of a control line displayed in the output signal area of the biological chromatographic test strip at least in part by determining an offset between a true channel brightness of the control line and a true channel brightness of the background fit section as represented by a depth of a trough associated with the true channel brightness of the control line, (ii) an intensity of a hook line displayed in the output signal area of the biological chromatographic test strip based on an intensity offset between one or more attributes of the hook line and the intensity of the background fit section at least in part by determining an offset between a true channel brightness of the hook line and the true channel brightness of the background fit section as represented by a depth of a trough associated with the true channel brightness of the hook line, and (iii) an intensity of a test line displayed in the output signal area of the biological chromatographic test strip at least in part by determining an offset between a true channel brightness of the test line and a true channel brightness of the background fit section as represented by a depth of a trough associated with the true channel brightness of the test line, wherein respective offsets determined for the control line, the hook line, and the test line are determined for each color channel of a red-green-blue (RGB) color space and summed to obtain a full-color delta for each respective line;

determine, based on the intensity of the hook line, that a test sample submitted via the biological chromatographic test strip is of a sufficient concentration to perform analysis with respect to a target analyte in the test sample;

based on the determination that the test sample submitted via the biological chromatographic test strip is of the sufficient concentration to perform the analysis with respect to the target analyte in the test sample, determine a relative intensity between the test line and at least one of the hook line or control line using the intensity of the test line and at least one of the intensity of the hook line or the intensity of the control line; and determine, based on the relative intensity, a concentration of the target analyte in the test sample submitted via the biological chromatographic test strip; and an interface in communication with the processing circuitry, the interface being configured to output data indicative of the concentration of the target analyte in the test sample determined by the processing circuitry.

14. The apparatus of claim 13, wherein the mobile computing device is a smartphone, and wherein the camera hardware is included in one of a rear-facing camera of the smartphone or in a front-facing camera of the smartphone.

15. The apparatus of claim 13, wherein the interface is a touchscreen display.

16. The apparatus of claim 13, wherein an inner surface of the lightbox comprises a reflective surface configured to reflect light emitted by a light source positioned near lens hardware of the camera hardware.

17. The apparatus of claim 13, wherein an inner surface of the lightbox comprises a light cavity configured to provide backlighting of the biological chromatographic test strip.

18. The apparatus of claim 13, wherein the trained model is a trained neural network.

* * * * *